(12) United States Patent
Rondot et al.

(10) Patent No.: US 7,977,364 B2
(45) Date of Patent: Jul. 12, 2011

(54) INDAZOLES, BENZISOXAZOLES AND BENZISOTHIAZOLES AND THEIR USE AS ESTROGENIC AGENTS

(75) Inventors: Benoit Rondot, La Colle sur Loup (FR); Jean Lafay, Nice (FR); Paule Bonnet, Breil sur Roya (FR); Thierry Clerc, Vigoulet Auzil (FR); Igor Duc, Cannes (FR); Eric Duranti, Saint Laurent du Var (FR); Francois Puccio, Nice (FR); Jacqueline Shields, Nice (FR); Christian Blot, Saint Fargeau-Ponthierry (FR); Philippe Maillos, Labastide Saint Georges (FR)

(73) Assignee: Laboratoire Thermamex, Monaco (MC)

( * ) Notice: Subject to any disclaimer, the term of this patent is extended or adjusted under 35 U.S.C. 154(b) by 0 days.

(21) Appl. No.: 11/664,887

(22) PCT Filed: Oct. 14, 2005

(86) PCT No.: PCT/EP2005/055262
§ 371 (c)(1),
(2), (4) Date: Jul. 30, 2007

(87) PCT Pub. No.: WO2006/040351
PCT Pub. Date: Apr. 20, 2006

(65) Prior Publication Data
US 2009/0023779 A1    Jan. 22, 2009

(30) Foreign Application Priority Data
Oct. 14, 2004  (EP) .................................. 04292439

(51) Int. Cl.
*A61K 31/423*  (2006.01)
*A61K 31/416*  (2006.01)
*C07D 261/20*  (2006.01)
*C07D 231/56*  (2006.01)

(52) U.S. Cl. ..... 514/379; 514/403; 548/241; 548/361.1; 548/362.5

(58) Field of Classification Search .................. 514/321, 514/403, 379, 373; 548/362.5, 359.5, 241, 548/207, 209, 212, 361.5, 362.1; 546/209
See application file for complete search history.

(56) References Cited

U.S. PATENT DOCUMENTS

| | | | |
|---|---|---|---|
| 4,166,452 A | 9/1979 | Generales, Jr. | |
| 4,256,108 A | 3/1981 | Theeuwes | |
| 4,265,874 A | 5/1981 | Bonsen et al. | |
| 6,008,237 A * | 12/1999 | Sahoo et al. | 514/369 |
| 6,090,836 A * | 7/2000 | Adams et al. | 514/379 |
| 2002/0086891 A1 * | 7/2002 | Aebi et al. | 514/373 |
| 2002/0103229 A1 * | 8/2002 | Bhagwat et al. | 514/338 |
| 2003/0171412 A1 | 9/2003 | Malamas et al. | |
| 2003/0207927 A1 | 11/2003 | Malamas et al. | |
| 2003/0232828 A1 | 12/2003 | Bernotas et al. | |
| 2004/0110956 A1 | 6/2004 | Lesuisse et al. | |
| 2004/0132794 A1 | 7/2004 | Lesuisse et al. | |
| 2004/0180896 A1 * | 9/2004 | Munson et al. | 514/248 |
| 2006/0074122 A1 | 4/2006 | Lesuisse et al. | |
| 2007/0093479 A1 | 4/2007 | Lesuisse et al. | |
| 2007/0155735 A1 | 7/2007 | Lesuisse et al. | |
| 2008/0261997 A1 | 10/2008 | Lesuisse et al. | |

FOREIGN PATENT DOCUMENTS

| | | |
|---|---|---|
| EP | 0 882 029 A | 12/1998 |
| JP | 2001288175 A * | 10/2001 |
| WO | WO 97/28137 A1 * | 8/1997 |
| WO | WO 00/78312 A | 12/2000 |
| WO | WO 01/02369 A2 * | 1/2001 |
| WO | WO 02/098860 A | 12/2002 |
| WO | WO 03/101968 A | 12/2003 |
| WO | WO 2004/022544 | 3/2004 |
| WO | 2004/043354 A2 | 5/2004 |
| WO | 2004/043933 A1 | 5/2004 |
| WO | WO 2004/062662 | 7/2004 |

OTHER PUBLICATIONS

Rudolph et al., 1,2-Benzisothiazole 1,1-Dioxides. Synthesis of 3-Alkyl-(or Aryl-)1,2-benzisothiazole 1,1-Dioxides and Related Compounds, 1974, J.C.S. Perkin I, 2589-2594.*

Lala et al., Role of nitric oxide in tumor progression: Lessons from experimental tumors, Cancer and Metastasis Reviews (1998), 17, 91-106.*

Golub et al., Molecular Classification of Cancer: Class Discovery and Class Prediction by Gene Expression Monitoring, Science (1999), vol. 286, 531-537.*

Robert B. Layzer, Section Five—Degenerative Diseases of the Nervous System, Cecil Textbook of Medicine, 20th edition (1996), vol. 2, pp. 2050-2057.*

Antonio R. Damasio, Alzheimer's Disease and Related Dementias, Cecil Textbook of Medicine, 20th edition (1996), vol. 2, pp. 1992-1996.*

FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/index.html.*

(Continued)

*Primary Examiner* — Kamal Saeed
*Assistant Examiner* — Kristin Bianchi
(74) *Attorney, Agent, or Firm* — Hamre, Schumann, Mueller & Larson, P.C.

(57) ABSTRACT

The present invention relates to compounds of formula (I):

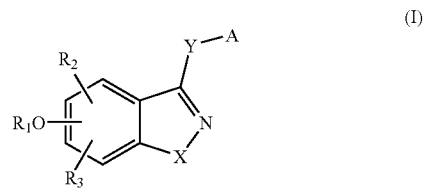

in which $R_1$, $R_2$, $R_3$, X, Y and A are as defined in the specification.

The compounds are modulators of the estrogen receptors.

5 Claims, No Drawings

OTHER PUBLICATIONS

X. Yang, et al. "Preparation and Acylation of Highly Functionalized Copper Derivatives of 3-Iodoindazoles Leading to Polyfunctional 3-Acylindazoles", Synlett, No. 13, Sep. 8, 2004, pp. 2303-2306.

Malamas, M. et al. "Design and Synthesis of Aryl Diphenolic Azoles as Potent and Selective Estrogen Receptor-beta-ligands", Journal of Medicinal Chemistry, No. 47, Aug. 9, 2004, pp. 5021-5040.

Burkman, R. "Hormone Replacement Therapy: Current Controversies", Minerva Ginecologica, vol. 55, No. 2, 2003, pp. 107-116.

Ramesh A. Bhat et al. "A Novel Human Estrogen Receptor β: Identification and Functional Analysis of Additional N-terminal Amino Acids." Journal of Steroid Biochemistry & Molecular Biology 67:3 (1998): 233-240.

Hemmie H.G. Berendsen et al. "Oestradiol and Mirtazapine Restore the Disturbed Tail-Temperature of Oestrogen-Deficient Rats." European Journal of Pharmacology 482 (2003): 329-333.

Brad R. Henke et al. "Optimization of 3-(1H-Indazol-3-ylmethyl)-1, 5-benzodiazepines as Potent, Orally Active CCK-A Agonists." J. Med. Chem. 40 (1997): 2706-2725.

Gerard Auclerc et al. "Management of Advanced Prostate Cancer." The Oncologist 5 (2000): 36-44.

C. Ainsworth. "Indazole Analog of Tryptamine: A New Synthesis of Indazoles." Am. Cham. Soc. 79 (1957): 5242-5245.

Tom O. Abney. "The Potential Roles of Estrogens in Regulating Leydig Cell Development and Finction: A Review." Steroids 64 (1999): 610-617.

Arthur M. Felix et al. "Rapid Removal of Protecting Groups from Peptides by Catalytic Transfer Hydrogenation with 1,4-Cyclohexadiene." J. Org. Chem. 43.21 (1978): 4194-4196.

Angela M. Brodie and Vincent C.O. Njar. "Aromatase Inhibitors and their Application in Breast Cancer Treatments." Steroids 65 (2000): 171-179.

Vincent C.O. Njar and Angela M.H. Brodie. "Comprehensive Pharmacology and Clinical Efficacy of Aromatase Inhibitors." Drugs 58:2 (1999): 233-255.

J. Botella et al. "Lack of Estrogenic Potential of Progesterone- or 19-Nor-progesterone-derived Progestins as Opposed to Testosterone or 19-Nor-testosterone Derivatives on Endometrial Ishikawa Cells." J. Steroid Biochem. Molec. Biol. 55:1 (1995): 77-84.

S.P.M. Crouch et al. "The Use of ATP Bioluminescence as a Measure of Cell Proliferation and Cytotoxicity." Journal of Immunological Methods 160 (1993): 81-88.

Shaun M. Cowley et al. "Estrogen Receptors α and β Form Heterodimers on DNA." The Journal of Biological Chemistry 272 (1997): 19858-19862.

John F. Course and Kenneth S. Kroach. "Estrogen Receptor Null Mice: What Have We Learned and Where Will They Lead Us?" Endocrine Reviews 20 (1999): 358-417.

Simon Chu and Peter J. Fuller. "Identification of a Splice Variant of the Rat Estrogen Receptor β gene." Molecular and Cellular Endocrinology 132 (1997): 195-199.

Haruhiko Sato et al. "Studies on Uricosuric Diuretics. II. Substituted 7,8-Dihydrofuro[2,3-g]-1,2-benzisoxazole-7carboxylic Acids and 7,8-Dihydrofuro[2,3-g]benzoxazole-7-carboxylic Acids." Chem. Pharm. Bull. 39:7 (1991): 1760-1772.

S. Carreau et al. "Topical Review: Sources of Oestrogen in the Testis and Reproductive Tract of the Male." International Journal of Andrology 22 (1999): 211-223.

Serdar E. Bulun et al. "Endocrine Disorders Associated with Inappropriately High Aromatase Expression." J. Steroid Biochem. Molec. Biol 61 (1997): 133-139.

G.R. Cunha et al. "Elucidation of a Role for Stromal Steroid Hormone Receptors in Mammary Gland Growth and Development Using Tissue Recombinants." Journal of Mammary Gland Biology and Neoplasia 2:4 (1997): 393-402.

J. Botella et al. "Structure-activity and Structure-Affinity Relationships of 19-Nor-progesterone Derivatives in Rat Uterus." J. Endocrinol. Invest. 13 (1990): 905-910.

Heather A. Harris et al. "Characterization of the Biological Roles of Estrogen Receptors, REα and ERβ, in Estrogen Target Tissues in Vivo through the Use of an ERα-Selective Ligand." Endocrinology 143:11 (2002): 4172-4177.

Heather A. Harris et al. "Evaluation of an Estrogen Receptor-β Agonist in Animal Models of Human Disease." Endocrinology 144:10 (2003): 4241-4249.

Hitoshi Uno et al. "Studies on 3-Substituted 1,2-Benzisoxazole Derivatives." Cham. Pharm. Bull. 24:4 (1976): 632-643.

H.L. Haller and P.S. Schaffer. "The Action of Isobutylmagnesium Bromide on 3,4,5-Trimethoxybenzonitrile." J Am Chem Soc 61 (1939): 2175-2177.

Stephen Green et al. "Human Oestrogen Receptor cDNA: Sequence, Expression and Homology to v-erb-A." Nature 320 (1986): 134-139.

E.B. Dennler and A.R. Frasca. "Synthesis of Indazoles using Polyphosohoric Acid-I." Tetrahedron 22 (1966): 3131-3141.

Elisabetta Teodori et al. "Synthesis and Binding Properties of Photoactivable Biotin-Conjugated Verapamil Derivatives for the Study of P-170 Glycoprotein." Bioorganic & Medicinal Chemistry 7 (1999) 1873-1880.

E.J. Corey. "Communications to the Editor: Protection of Hydroxyl Groups as tert-Butyldimethylsilyl Derivatives" Journal of the American Chemical Society 94:17 (1972): 6190-6191.

David M. Fink and Joseph T. Strupczewski. "Preparation of 6-Fluorobenzisothiazoles via a Regioselective Nucleophillic Aromatic Substitution Reaction." Tetrahedron Letters 34:41 (1993): 6525-6528.

Walter H. Hartung and Robert Simonoff. "Chapter 5: Hydrogenolysis of Benzyl Groups Attached to Oxygen, Nitrogen, or Sulfur." Organic Reactions (1953): 263-326.

L. Kangas et al. "Bioluminescence of Cellular ATPL A New Method for Evaluating Cytotoxic Agents in Vitro." Medical Biology 62 (1984): 338-343.

Kenneth L. Kees et al. "Synthesis and Antiallergic Activity of a Novel Series of 5-Lipoxygenase Inhibitors." J. Med. Chem 29 (1986): 2329-2334.

Kevin J. Duffy et al. "Hydrazinonaphthalene and Azonaphthalene Thrombopoietin Mimics Are Nonpeptidyl Promoters of Megakaryocytopoiesis." J. Med. Chem. 44 (2001) 3730-3745.

Kathleen I. Pritchard. "Current and Future Directions in Medical Therapy for Breast Carcinoma." Cancer 85 Suppl. 12 (2000): 3065-3072.

Michel Cyr et al. "Estrogenic Modulation of Brain Activity: Implications for Schizophrenia and Parkinson's Disease." Revue de Psychiatrie & de Neuroscience 27 (2002): 12-27.

J.F.W. McOmie et al. "Demethylation of Aryl Methyl Ethers by Boron Tribromide." Tetrahedron 24 (1968): 2289-2292.

John Y.L. Chung et al. "Friedel-Crafts Cyclization of 2-(3-Indolythio)propionic Acids. An Unusual Rearrangement Leading to 4-Sulfur-Substituted Tricyclic Indoles." Tetrahedron Letters 33:33 (1992) 4717-4720.

M.A. Elkasby and M.A.I. Salem. "Synthesis of New Isoxazoles from Isoxazolines, Chalkones, Chalkone Dibromides, Epoxides & Acetylated Ketoximes & Their Conversion into Novel Heterocycles." Indian Journal of Chemistry 19B (1980): 571-575.

George G.J.M. Kuiper et al. "Comparison of the Ligand Binding Specificity and Transcript Tissue Distribution of Estrogen Receptors α and β." Endocrinology 138:3 (1997): 863-870.

Sudha Warder Mitra et al. "Immunolocalization of Estrogen Receptor β in the Mouse Brain: Comparison with Estrogen Receptor α." Endocrinology 144:5 (2003) 2055-2067.

Donald P. McDonnell. "Selective Estrogen Receptor Modulators (SERMs): A First Step in the Development of Perfect Hormone Replacement Therapy Regimen." J Soc Gynecol Investig 7:1 (2000) S10-S15.

Martin R. Tremblay et al. "Spironolactone-related Inhibitors of Type II 17β-Hydroxysteroid Dehydrogenase: Chemical Synthesis, Receptor Binding Affinities, and Proliferative/Antiproliferative Activities." Bioorganic & Medicinal Chemistry 7 (1999): 1013-1023.

Masayuki Kitagawa et al. "Aryloxyacetic Acid Diuretics with Uricosuric Activity. II. Substituted [(4-Oxo-1-benzopyran-7-yl)oxy]acetic Acids and the Related Compounds." Chem. Pharm. Bull. 39:10 (1991): 2681-2690.

Marvin J. Meyers et al. "Estrogen Receptor-β Potency-Selective Ligands: Structure-Activity Relationship Studies of Diarylpropionitriles and their Acetylene and Polar Analogues." J. Med. Chem, 44 (2001): 4230-4251.

Bruce A. Littlefield et al. "A Simple and Sensitive Mircotiter Plate Estrogen Bioassay Based on Stimulation of Alkaline Phosphatase in Ishikawa Cells: Estrogenic Action of Δ5 Adrenal Steroids." Endrocrinology 127:6 (1990): 2757-2762.

George G.J.M. Kuiper et al. "Colning of a Novel Estrogen Receptor Expressed in Rat Prostate and Ovary." Proc. Natl. Acad. Sci. USA 93 (1996): 5925-5930.

George G.J.M. Kuiper et al. "Interaction of Estrogenic Chemicals and Phyotoestrogens with Estrogen Receptor β." Endocrinology 139:10 (1998): 4252-4263.

Sietse Mosselman et al. "ERβ: Identification and Characterization of a Novel Human Estrogen Receptor." FEBS Letters 392 (1996): 49-53.

Roger D. Porsolt et al. "Behavioral Dispair in Rats: A New Model Sensitive to Antidepressant Treatments." European Journal of Pharmacology 47 (1978): 379-391.

Ashley C.W. Pike et al. "Structure of the Ligand-Binding Domain of Oestrogen Receptor Beta in the Presence of a Partial Agonist and a Full Agonist." The European Molecular Biology Organization Journal 18:17 (1999) 4608-4618.

Russell D. Petty et al. "Comparison of MTT and ATP-Based Assays for the Measurement of Viable Cell Number." J. Biolumin Chemilumin 10 (1995) 20-34.

Theo Pelzer et al. "Estrogen Effects in the Miyocardium: Inhibition of NF-κB DNA Binding by Estrogen Receptor-α and -β." Biochemical and Biophysical Research Communications 286 (2001): 1153-1157.

C. Palmieri et al. "Estrogen Receptor Beta in Breast Cancer." Endocrine-Related Cancer 9 (2002): 1-19.

Peter Nussbaumer et al. "2-Substituted 4-(Thio)chromenone 6-O-Sulfamates: Potent Inhibitors of Human Steroid Sulfatase." J. Med. Chem 45 (2002): 4310-4320.

Peter M. Kendall. "Synthetic Route to an Aromatic Analogue of Strigol." J. Org. Chem 44:9 (1979): 1421-1424.

Makoto Okkada et al. "Efficient General Method for Sulfamoylation of a Hydroxyl Group." Tetrahedron Letters 41 (2000): 7047-7051.

Stefan Nilsson et al. "Mechanisms of Estrogen Action." Psychological Review 81:4 (2001):1535-1535.

Monique E. Quaedackers et al. "4-Hydroxytamoxifen Trans-Represses Nuclear Factor-κB Activity in Human Osteoblastic U2-OS Cells Through Estrogen Receptor (ER)α, and Not Through ERβ." Endocrinology 142:3 (2001): 1156-1166.

Zhang Weihua et al. "A Role for Estrogen Receptor β in the regulation of Growth of the Ventral Prostate." Proceedings of the National Academy of Sciences of the United States of America 98:11 (2001): 6330-6335.

Nobuhide Watanabe et al. "Discovery and Preclinical Characterization of (+)-3-[4-(1-Piperidinoethoxy)phenyl]spiro [indene-1,1'-indane]-5,5'-diol Hydrochloride: A Promising Nonsteroidal Estrogen Receptor Agonist for Hot Flush." J. Med. Chem. 46 (2003): 3961-3964.

Charles L. Vogel. "Update on the Current Use of Hormonals as Therapy in Advanced Breast Cancer." Anti-Cancer Drugs 14:4 (2003): 265-273.

Ulrich Lerch and Johann Konig. "Selective Alkylation of Ohenylhydrazine: A Facile and Efficient Synthesis of 1-Alkyl-1-phenlyhydrazines." Synthesis 2 (1983): 157-158.

C. Dominique Torran-Allerand. "Minireview: A Plethora of Estrogen Receptors in the Brain: Where Will It End?" Endocrinology 145:3 (2004): 1069-1074.

Deborah Witte et al. "Estrogen Receptor β is Expressed in Human Colorectal Adenocarcinoma." Human Pathology 32:9 (2001): 940-944.

Yoshinori Yamanaka et al. "Synthesis of Benzylaminopyrimidines and Their Fungicidal Activities against Wheat Brown Rust and Barley Powder Mildew." Pestic Sci. 54 (1998): 223-229.

Elena V. Zoubina and Peter G. Smith. "Expression of Estrogen Receptors α and β by Sympathetic Ganglion Neurons Projecting to the Proximal Urethra of Female Rats." Journal of Urology 169 (2003): 382-385.

Wojciech Krezel et al. "Increased Anxiety and Synaptic Plasticity in Estrogen Receptor β-deficient Mice." Proceedings of the National Academy of Sciences of the United States of America 98:21 (2001): 12278-12282.

Maryvonne Warembourg and Daniele Leroy. "Comparative Distribution of Estrogen Receptor α and β Immunoreactivities in the Forebrain and the Midbrain of the Female Guinea Pig." Brain Research 1002 (2004): 55-66.

Gil-Jin Shim et al. "Disruptionof the Estrogen Receptor β Gene in Mice Causes Myeloproliferative Disease Resembling Chronic Myeloid Leukemia With Lymphoid Blast Crisis." Proceedings of the National Academy of Sciences of the United States of America 100:11 (2003): 6694-6699.

Andrew K. Shiae et al. "The Structural Basis of Estrogen Receptor/Coactivator Recognition and the Antagonism of This Interaction by Tamoxifen." Cell 95 (1998): 927-937.

Janos Szabo et al. "Ring Transformations of 1,3-Benzothiazines, 51 Synthesis of Benzisothiazoles by the Oxidative Ring Contraction of 2-Aryl-4H- and 4-Aryl-2H-1, 3-Benzothiazines." Tetrahedron 44:10 (1988): 2985-2992.

Hironobu Sasano and Nibuhiro Hirada. "Intratumoral Aromatase in Human Breast, Endometrial, and Ovarian Malignancies." Endocrine Reviews 19:5 (1998): 593-607.

F. Sciarra and V. Toscano. "Role of Estrogens in Human Benign Prostatic Hyperplasia." Archives of Andrology 44 (2000): 213-220.

Tadao Ishizuka and Takshisa Kunieda. "Mild and Selective Ring-Cleavage of Cyclic Carbmates to Amino Alcohols." Tetrahedron Letters 28:36 (1987): 1485-4188.

Spiros Grivas and Erik Ronne. "Facile Desulfurization of Cyclic Thioureas by Hydrogen Peroxide in Acetic Acid." Acta Chemica Scandinuvica 49 (1995): 225-229.

Evs Bhushana Rao et al. "Synthesis of 7-Actyl-6-hydroxy-3-substituted-1, 2-benzisoxazoles & Their Conversion into Other Heterocycles." Indian Journal of Chemistry 26B (2987): 620-623, 1987.

Shaun S. Stauffer et al. "Pyrazole Ligands: Structure-Affinity/Activity Relationships and Estrogen Receptor-α-Selective Agonists." J. Med. Chem 43 (2000): 4934-4947.

TA10TA-F40, "R&TTE Declaration of Conformity (DoC)" Data Sciences International, 1999.

Oyo Mitsunobu. "The Use of Diethyl Azodicarboxylate and Triphenylphosphine in Synthesis and Transformation of Natural Products." Synthesis 1 (1981): 1-28.

* cited by examiner

ововStates Patent US 7,977,364 B2

INDAZOLES, BENZISOXAZOLES AND BENZISOTHIAZOLES AND THEIR USE AS ESTROGENIC AGENTS

FIELD OF THE INVENTION

The present invention relates to non steroidal compounds with affinity for estrogen receptors. More specifically, the invention relates to indazole, benzisoxazole and benzisothiazole compounds as estrogen receptor subtype modulators and/or selective estrogen receptor modulators (SERM). The present invention also relates to pharmaceutical compositions containing these compounds, and to the use of these compounds in the treatment of estrogen-related diseases.

BACKGROUND OF THE INVENTION

The end of the reproductive years of a person's life can often be accompanied by uncomfortable and disruptive symptoms, one of the most common of which is hot flushes. Perimenopause, or premenopause, is the period of years in which normal ovulatory cycles give way to cessation of menses. This time is marked by irregular menstrual cycles. Cycle length begins to increase, and ovulation and fertility decrease. Menopause is typically defined as the point, after the loss of ovarian activity, when permanent cessation of menstruation occurs. In addition, estrogens are involved in various other physiological processes such as the modulation of the immune response and development of cancer (breast, endometrium, colon, prostate). ERα has been proven to be implicated in several diseases, such as breast cancer, and osteoporosis.

It is well established that estrogens play an important role in the development and homeostasis of the reproductive, central nervous, skeletal and cardiovascular systems in both males and females. To date, a plethora of estrogen receptors have been discovered in the brain, involved in various processes such as mood, temperature regulation, sleep, susceptibility to seizure, pain mechanism, and cognitive functions (Toran-Allerand, Endocrinology, 2004, 145, 1069-1074).

Currently, the estrogen receptor (ER) is a nuclear receptor with two known different subtypes. A new subtype ERβ, different from the known ERα subtype (Green, Nature, 1986, 320, 134-139), was recently discovered (Mosselman et al, FEBS Letters, 1996, 392, 49-53). These subtypes have different biological roles and may have selective and effective clinical uses (Harris H. A., Endocrinology, 2002, 143, 11, 4172-4177). ER subtypes share about 50% identity in the ligand-binding domain (Kuiper et al, Endocrinology, 1998, 139(10), 4252-4263), they have similar Estradiol ($E_2$) binding affinities and can hetero- or homodimerize (Cowley, J Biol Chem, 1997, 272, 19858-19862) to form a signalling complex (Kuiper et al, Endocrinology, 1997, 138(10), 863-870; Kuiper, Proc. Natl. Acad. Sci. USA, 1996, 93, 5925-5930). ERβ is strongly expressed in a number of tissues including prostate epithelium (Weihua Z, Proc. Natl. Acad. Sci. USA, 2001, 98, 6330-6335), sympathetic ganglia (Zoubina E. V., J. Urol., 2003, 169, 382-385), colon (Witte D., Hum. Pathol., 2001, 32, 940-944), bladder, ovarian granulosa cells (Nilsson S., Physiol. Rev., 2001, 81, 1535-1565), bone marrow (Shim G. J., Proc. Natl. Acad. Sci. USA, 2003, 100, 6694-6699), breast stroma (Cunha G. R., J. Mammary Gland Biol. Neoplasia, 1997, 2, 393-402), lung, intestine, vascular endothelium, dorsal raphe, parts of the brain (Mitra S. W., Endocrinology, 2003, 144, 2055-2067, Krel W., Proc. Natl. Acad. Sci. USA, 2001, 98, 12278-12282). ERα is expressed in breast epithelium (Palmieri C., Endocr. Relat. Cancer, 2002, 9, 1-13), uterus, bone, ovary theca cells (Couse J., Endocr. Rev., 1999, 20, 358-417), prostate stroma (Chu S., Mol. Cell Endocrinol., 1997, 132, 195-199), liver, testis. The finding of compounds with a specific affinity for one or the other subtypes could provide a selective treatment of estrogen-related diseases such as Alzheimer's disease, menopausal complaints (e.g. hot flushes, vaginal dryness, atrophy), cognitive functions (e.g. anxiety, depression, dementia), osteoporosis, estrogen dependent tumours (uterine, breast, colon, or prostate cancers), benign prostatic hyperplasia, bladder control, hearing disorders, stroke, leukaemia, hypertension, obesity, irritable bowel syndrome, or reproductive aspects such as contraception or infertility. ERβ-selective ligands may be therapeutically useful agents to treat chronic intestinal and joint inflammation (Harris et coll., Endocrinology, 2003, 144, 4241-4249).

According to Warembourg M and Leroy D (Brain Res., 2004, 26; 55-66), ERβ was only detected within the rat dorsal raphe nucleus. In contrast, only ERα-immunoreactivity was seen in the septum, and in the magnocellular supraoptic, paraventricular, arcuate, and premammillary nuclei. These observations provide evidence of a distinct neuroanatomical pattern for the two subtypes of the ERs. Localisation of ERβ in serotonin cells show the link between ERβ and the serotoninergic pathway. Finally, Cyr M et al. described (J Psychiatry Neurosci., 2002, 27, 12-27) the effect of a selective estrogen receptor modulator (SERM) such as raloxifen on 5-HT2a receptor.

In conclusion it seems to be relevant to develop ERβ modulators as compounds of interest in the field of schizophrenia, neurodegenerative diseases such a Alzheimer's disease or Parkinson's disease. For the same reasons, ERβ modulators should be of interest as neuroprotective, antidepressant or anxiolytic agents.

However, the two receptors which act as ligand activated transcription factors, were found in a variety of tissues, and differed in their binding pocket only by two amino acids: Leu and Met in ERα, Met and Ile in ERβ. Those similarities could explain that the control of the subtype alpha or beta led to the same pharmacological effect, as it is the case in preclinical model of hot flush phenomena. While ERα modulator decreased the occurrence of hot flushes in a rat preclinical model (Harris et al., Endocrinology, 2002, 143, 4172-4177), selective estrogen receptor modulators such as spiroindene compounds, which were affine for both subtypes, had the same effect on hot flushes (Watanabe et al., J Med Chem, 2003, 46, 3961-3964).

It has also been shown that estrogen receptors can suppress NFKB-mediated transcription in both a ligand-dependent and independent manner (Quaedackers, et al., Endocrinology 2001, 142: 1156-1166; Bhat, et al., Journal of Steroid Biochemistry & Molecular Biology 1998, 67: 233-240; Pelzer, et al., Biochemical & Biophysical Research Communications 2001, 286: 1153-7). These data show the link between selective estrogen receptor modulators and NFKB which is implicated in apoptosis and immune/inflammatory response.

Many compounds have been described as estrogen receptor agonists or antagonists as they respectively had a similar activity or blocked the activity of estradiol. Such agonist compounds could be used as contraceptive agents in premenopausal women. Antagonists are widely used therapeutic agents in the treatment of breast cancer (Vogel, Anticancer Drugs, 2003, 14, 265-273) whereas agonists are used in HRT (Hormone Replacement Therapy) in post menauposal women (Burkman, Minerva Ginecol, 2003, 55, 107-116) to treat hot flushes, vaginal atrophy. SERMs are compounds that present mixed activities depending on the tissue (McDonnell, J Soc Gynecol Invest, 2000, 7, S10-S15). SERMs might have utility for the treatment of osteoporosis, cardiovascular diseases and related estrogen receptor diseases.

Estrogen receptors adopt different conformations when binding ligands. Three-dimensional structures of ERα and ERβ have been solved by co-crystallisation with various ligands (Pike A. C. W., EMBO J, 1999, 18, 4608-4618; Shiau A. K., Cell, 1998, 95, 927-937). Each ligand influences receptor ERα or ERβ conformations, leading to distinct biological activities.

Various compounds presented as estrogenic agents have been described in US 2003/0207927 A1 and US 2003/0171412 A1. Indazole derivatives presented as potassium channel blockers are described in WO 2004/043354 and WO 2004/043933. The synthesis of various isoxazoles is described in Ind J Chem 1980, 19B: 571-575. Benzisoxazole intermediates used in the preparation of diuretic compounds are described in Chem Pharm Bull 1991, 39(7): 1760-1772. The synthesis of various benzisothiazoles is described in Tetrahedron 1988, 44(10): 2985-2992.

SUMMARY OF THE INVENTION

One aspect of this invention is to provide indazole, benzisoxazole and benzisothiazole compounds, which have an affinity for the estrogen receptors. Another aspect of this invention is to provide a pharmaceutical composition containing an indazole, benzisoxazole or benzisothiazole compound as mentioned above.

A further aspect of this invention is to provide the use of an indazole, benzisoxazole, or benzisothiazole compound in the manufacture of a medicament for treating or preventing various diseases mediated by estrogen receptors.

The indazole, benzisoxazole or benzisothiazole compounds of this invention can be represented by the following general formula (I):

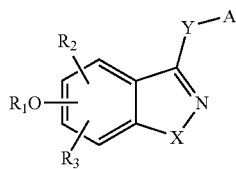

(I)

wherein:
$R_1$ is hydrogen or a $(C_1-C_6)$alkyl, $(C_3-C_6)$cycloalkyl, trifluoromethyl, —N=$CR_5R_6$, —$SO_2NR_7R_8$, phenyl, phenyl$(C_1-C_3)$alkyl or $(C_1-C_3)$alkyl substituted by a saturated heterocyclic radical, wherein the phenyl is unsubstituted or substituted by at least one substituent selected from the group consisting of a hydroxyl, a halogen, a nitro, a cyano, a $(C_1-C_3)$alkyl, a $(C_1-C_3)$alkoxy and a trifluoromethyl; $R_1$ can also be a salt;
$R_2$ and $R_3$ are each independently hydrogen or a hydroxyl, halogen, nitro, cyano, $(C_1-C_6)$alkyl, $(C_3-C_6)$cycloalkyl, $(C_1-C_6)$alkoxy, trifluoromethyl, —$NR_7R_8$, —$CONR_7R_8$, —$COR_9$ or —$CO_2R_9$ group; $R_2$ can also be a phenyl or a saturated or unsaturated heterocycle, wherein the phenyl is unsubstituted or substituted by at least one substituent selected from the group consisting of a hydroxyl, a halogen, a nitro, a cyano, a $(C_1-C_3)$alkyl, a $(C_1-C_3)$alkoxy, a trifluoromethyl and a saturated heterocyclic radical;
X is O, S, SO, $SO_2$ or $NR_4$;
$R_4$ is hydrogen or a $(C_1-C_6)$alkyl, $(C_3-C_6)$cycloalkyl, phenyl, phenyl$(C_1-C_3)$alkyl, $(C_1-C_3)$alkyl substituted by a saturated heterocyclic radical, —$COR_7$, —$CO_2R_7$ or —$SO_2NR_7R_8$ group, wherein the phenyl is unsubstituted or substituted by at least one substituent selected from the group consisting of a hydroxyl, a halogen, a nitro, a cyano, a $(C_1-C_3)$alkyl, a $(C_1-C_3)$alkoxy, a trifluoromethyl, a phenyl$(C_1-C_3)$alkyl and a phenyl$(C_1-C_3)$alkoxy;
Y is direct bond, O, S, SO, $SO_2$, $NR_4$, CO, —$(CR_{10}R_{11})_n$— or —$R_{10}C$=$CR_{11}$—;

$R_5$, $R_6$, $R_7$ and $R_8$ are each independently hydrogen or a $(C_1-C_6)$alkyl or $(C_3-C_6)$cycloalkyl group;
$R_9$ is hydrogen, a $(C_1-C_6)$alkyl, a phenyl or a saturated or unsaturated heterocyclic radical, wherein the phenyl is unsubstituted or substituted by at least one substituent selected from the group consisting of a hydroxyl, a halogen, a nitro, a cyano, a $(C_1-C_3)$alkyl, a $(C_1-C_3)$alkoxy, a trifluoromethyl and a saturated heterocyclic radical;
$R_{10}$ and $R_{11}$ are each independently hydrogen or a cyano, $(C_1-C_6)$alkyl, —CO-phenyl, —CO(unsaturated heterocyclic radical) or —$CONR_7R_8$ group, wherein the phenyl is unsubstituted or substituted by at least one substituent selected from the group consisting of a hydroxyl, a halogen, a nitro, a cyano, a $(C_1-C_3)$alkyl, a $(C_1-C_3)$alkoxy and a trifluoromethyl;
n is 1 or 2;
A is a $(C_3-C_{15})$cycloalkyl, a $(C_3-C_{15})$cycloalkene, a phenyl or a naphthyl, wherein the cycloalkyl or the cycloalkene is unsubstituted or substituted by at least one $(C_1-C_6)$alkyl, and wherein the phenyl or the naphthyl is unsubstituted or substituted by at least one substituent selected from the group consisting of a hydroxyl, a halogen, a nitro, a cyano, a $(C_1-C_3)$alkyl, a $(C_1-C_3)$alkoxy and a trifluoromethyl;
when X is $NR_4$, Y and $R_2$ together with the indazole ring bearing them can also form a 1H-pyrano[4,3,2-cd]indazole.

The compounds of formula (I) are claimed as such except that:
1/ when X is O, S or $NR_4$, $R_1$ is hydrogen or a $(C_1-C_6)$alkyl, $(C_3-C_6)$cycloalkyl or trifluoromethyl, and Y is a direct bond, then A is not optionally substituted phenyl or optionally substituted naphthyl;
2/ when X is $NR_4$ where $R_4$ is H or $(C_1-C_6)$alkyl and $R_1O$ is 6-$OCH_3$, then Y is not CO;
3/ when X is O, $R_1O$ is 6-OH or 6-$OCH_3$, Y is a direct bond and A is cyclopentyl, then ($R_2$, $R_3$) or ($R_3$, $R_2$) is different from (H, Cl) in position 4, 5;
4/ when X is O, $R_1O$ is 6-OH, $R_2$ and $R_3$ are H and Y is CH=CH, then A is not phenyl or 4-methoxyphenyl;
5/When X is $SO_2$, A is phenyl and $R_1O$ is 5- or 6-$OCH_3$, then ($R_2$, $R_3$) or ($R_3$, $R_2$) is different from (H, $OCH_3$) in position 6- or 5-.

In the description and claims, the term "$(C_1-C_6)$alkyl" is understood as meaning a linear or branched hydrocarbon chain having 1 to 6 carbon atoms. A $(C_1-C_6)$alkyl radical is for example a methyl, ethyl, propyl, isopropyl, butyl, isobutyl, tert-butyl, pentyl, isopentyl or hexyl radical. Preferred alkyl radicals are those having 1, 2 or 3 carbon atoms.

The term "halogen" is understood as meaning a chlorine, bromine, iodine or fluorine atom.

The term "$(C_3-C_{15})$cycloalkyl" is understood as meaning a saturated, fused or bridged, mono-, bi- or tricyclic hydrocarbon having 3 to 15 carbon atoms. A monocyclic radical is for example a cyclopropyl, cyclopentyl, cyclohexyl, cycloheptyl, cyclooctyl or cyclododecyl radical. A fused, bridged or spiranic, dicyclic or tricyclic radical is for example a norbornyl, bornyl, isobornyl, noradamantyl, adamantyl or spiro[5,5]undecanyl radical. Preferred cycloalkyls are those having 5 to 12 carbon atoms, the cyclopentyl, cyclohexyl, cycloheptyl and adamantyl radicals being especially preferred. A $(C_3-C_6)$cycloalkyl radical is for example a cyclopropyl, cyclobutyl, cyclopentyl or cyclohexyl radical.

The term "$(C_3-C_{15})$cycloalkene" is understood as meaning an unsaturated $(C_3-C_{15})$cycloalkyl, the latter term being as defined above.

The term "$(C_1-C_6)$alkoxy" is understood as meaning a group OR in which R is a $(C_1-C_6)$alkyl as defined above. A $(C_1-C_6)$alkoxy radical is for example a methoxy, ethoxy, propoxy, isopropoxy, butoxy, isobutoxy, tert-butoxy, n-pentyloxy or isopentyloxy radical. Preferred alkoxy radicals are those having 1, 2 or 3 carbon atoms.

In the definition of $R_1$, a "salt" is understood as meaning an alkali metal salt or alkaline earth metal salt, such as a sodium, potassium, magnesium or calcium salt, or a salt with an ammonium or with an organic amine such as triethylamine, ethanolamine or tris-(2-hydroxyethyl)amine.

The term "heterocycle" or "heterocyclic", is understood as meaning a saturated or unsaturated 5- to 8-membered monocyclic radical containing one or two heteroatoms chosen from O, N and S.

Examples of unsaturated heterocyclic radicals include, but are not limited to, the furyl, imidazolinyl, imidazolyl, pyridyl, pyrazinyl, pyrazolyl, pyridazinyl, pyrimidinyl, pyrrolyl, quinolinyl, isoquinolinyl, thiazolyl, thienyl benzimidazolyl, benzoxazolyl, benzothiazolyl, indolyl and indazolyl radicals.

Examples of saturated heterocyclic radicals include, but are not limited to, the imidazolidinyl, morpholinyl, thiomorpholinyl, piperidyl, piperazinyl, pyrrolidinyl, pyrazolidinyl, tetrahydrofuryl, 2-oxopiperazinyl, 2-oxopiperidyl and 2-oxopyrrolidinyl radicals, the morpholinyl and piperidyl radicals being preferred. Needless to say, when X is $NR_4$ and Y and $R_2$ together form with the indazole ring bearing form a 1H-pyrano[4,3,2-cd]-indazole, one of the carbon atom of the "pyrano moiety" bears substituent A as defined above.

The compounds of formula (I) can form addition salts with acids. Such salts, especially those which are pharmaceutically acceptable, are encompassed by the present invention. Examples of salts include those formed, for example with inorganic acids such as hydrochloric acid, hydrobromic acid, sulfuric acid, nitric acid, phosphoric acid, or with organic carboxylic acids such as acetic acid, propionic acid, glycolic acid, pyruvic acid, oxalic acid, malic acid, fumaric acid, tartaric acid, citric acid, benzoic acid, cinnamic acid, mandelic acid, methanesulfonic acid.

The present invention also encompasses stereoisomeric forms of the compounds of formula (I).

Preferred compounds of formula (I) include those that fulfil at least one of the following conditions:

$R_1$ is hydrogen, a $(C_1-C_6)$alkyl, a phenyl$(C_1-C_3)$alkyl, a $(C_1-C_3)$alkyl substituted by a saturated heterocyclic radical or a —$SO_2NR_7R_6$ group;
$R_2$ is hydrogen, hydroxyl, $(C_1-C_6)$alkyl or halogen;
$R_3$ is hydrogen;
Y is direct bond;
A is a $(C_3-C_{15})$cycloalkyl optionally substituted by at least one $(C_1-C_6)$alkyl;
$R_1O$ is in position 6- of the ring.

Particularly preferred compounds are those wherein:
$R_1$ is hydrogen or a —$SO_2NR_7R_8$ group in which $R_7$ and $R_8$ are each independently hydrogen or a $(C_1-C_6)$alkyl;
$R_2$ is hydrogen;
A is a $(C_3-C_{12})$cycloalkyl optionally substituted by 1 to 4 $(C_1-C_6)$alkyls.

The following compounds are also preferred:
a) Compounds where X is $NR_4$ and
$R_1$ is hydrogen or a $(C_1-C_6)$alkyl, phenyl$(C_1-C_3)$alkyl or —$SO_2NR_7R_8$ group;
$R_2$ and $R_3$ are each hydrogen;
$R_4$ is hydrogen or a $(C_1-C_6)$alkyl, phenyl, phenyl$(C_1-C_3)$alkyl, $(C_1-C_3)$alkyl substituted by a saturated heterocyclic radical, —$SO_2NR_7R_8$ or —$COR_9$ group, where the phenyl is optionally substituted by at least one substituent selected from the group consisting of a hydroxyl, a halogen and a phenyl$(C_1-C_3)$alkoxy;
Y is a direct bond, —$(CR_{10}R_{11})_n$— or —$R_{10}C=CR_{11}$;
$R_7$ and $R_8$ are each independently hydrogen or a $(C_1-C_6)$alkyl;
$R_9$ is hydrogen or a $(C_1-C_6)$alkyl;

$R_{10}$ and $R_{11}$, are each independently hydrogen, cyano or a —$CONR_7R_8$ group;
n is 1 or 2;
A is a $(C_3-C_{15})$cycloalkyl optionally substituted by at least one $(C_1-C_6)$alkyl or a phenyl optionally substituted by a hydroxyl or a $(C_1-C_3)$alkoxy;
Y and $R_2$ together with the indazole ring bearing them can also form a 1H-pyrano[4,3,2-cd]indazole;
provided that when $R_1$ is H or $(C_1-C_6)$alkyl and Y is a direct bond, then A is not optionally substituted phenyl.

b) Compounds where X is O and
—$R_1$ is hydrogen or a $(C_1-C_6)$alkyl, phenyl$(C_1-C_3)$alkyl, $(C_1-C_3)$alkyl substituted by a saturated heterocyclic radical or —$SO_2NR_7R_8$ group;
$R_2$ is hydrogen, halogen, hydroxyl or $(C_1-C_6)$alkoxy;
$R_3$ is hydrogen;
Y is a direct bond, —$(CR_{10}R_{11})_n$ or —$CR_{10}=CR_{11}$—;
$R_7$ and $R_8$ are each independently hydrogen or $(C_1-C_6)$alkyl;
$R_{10}$ and $R_{11}$ are each independently hydrogen or cyano;
n is 1 or 2;
A is a $(C_3-C_{15})$cycloalkyl optionally substituted by at least one $(C_1-C_6)$alkyl or a phenyl optionally substituted by at least one substituent selected from $(C_1-C_3)$alkoxy, hydroxyl, $(C_1-C_3)$alkyl and halogen;
provided that
b1/ when $R_1$ is H or $(C_1-C_6)$alkyl and Y is a direct bond, then A is not optionally substituted phenyl;
b2/ when $R_1O$ is 6-OH or 6-$OCH_3$, Y is a direct bond and A is cyclopentyl, then $(R_2, R_3)$ is different from (Cl, H) in position 4, 5;
b3/ when X is O, $R_1O$ is 6-OH, $R_2$ and $R_3$ are H and Y is CH=CH, then A is not phenyl or 4-methoxyphenyl;

c) Compounds where X is $S(O)_m$ and
$R_1$ is hydrogen or a phenyl$(C_1-C_3)$alkyl or —$SO_2NR_7R_8$ group;
$R_2$ and $R_3$ are each hydrogen, hydroxyl or halogen;
Y is a direct bond, —$(CR_{10}R_{11})_n$ or —$CR_{10}=CR_{11}$—;
$R_7$ and $R_8$ are each independently hydrogen or a $(C_1-C_6)$alkyl;
$R_{10}$ and $R_{11}$ are each independently hydrogen or cyano;
A is a $(C_3-C_{15})$cycloalkyl optionally substituted by at least one $(C_1-C_6)$alkyl;
m is 0, 1 or 2.

In view of their capability to act as agonists or antagonist for estrogen receptors (in other words as SERMs), the compounds of the invention can be used alone or in combination with other active ingredients for the treatment or the prevention of any estrogen-dependent disorder or for the management of estrogen-regulated reproductive functions, in humans (Njar V C and Brodie A M, Drugs, 1999, 58: 233-255) as well as in wild or domestic animals.

The breasts being sensitive targets of estrogen-stimulated proliferation and/or differentiation, SERMs are especially useful in the treatment or prevention of benign breast diseases in women, gynecomastia in men and in benign or malignant breast tumors with or without metastasis both in men and women (A. M. Brodie and V. C. Njar, Steroids, 2000, 65: 171-179; K. I. Pritchard, Cancer, 2000, 85, suppl 12: 3065-3072), or in male or female domestic animals.

Due to the involvement of estrogens in the mechanisms of ovulation, implantation and pregnancy, SERMs according to the invention can be used, respectively, for contraceptive, contragestive or abortive purposes in women (A. M. Brodie and V. C. Njar, Drugs, 1999, 58: 233-255) as well as in females of wild or domestic animal species.

The uterus is another reproductive organ responsive to estrogenic stimulation. SERMs are therefore useful to treat or prevent endometriosis, benign uterine diseases or benign or malignant uterine tumors with or without metastasis in women (A. M. Brodie and V. C. Njar, Drugs, 1999, 58: 233-255) or in female domestic animals.

The ovary being the physiological source of estrogen, SERMs can be used to treat abnormal or untimely ovarian estrogen production such as polycystic ovary syndrome or precocious puberty, respectively (Bulun et al., J Steroid Biochem Mol Biol, 1997, 61: 133-139). Ovarian as well as non-ovarian but estrogen-producing benign or malignant tumors with or without metastasis (Sasano H and Harada N, Endocrine Reviews, 1998, 19: 593-607) may also benefit from treatment with SERMs according to the invention.

In males, prostate and testicular tissues are also responsive to estrogenic stimulation (Abney T O, Steroids, 1999, 64: 610-617; Carreau S et al., Int J Androl, 1999, 22: 133-138). Therefore, SERMs can be used to treat or to prevent benign (Sciarra F and Toscano V, Archiv Androl, 2000, 44: 213-220) or malignant prostate tumors with or without metastasis (Auclerc G et al., Oncologist, 2000, 5: 36-44) or to treat, prevent or control spermatogenesis functions or malfunctions, in men as well as in male wild or domestic animals.

Estrogens are also known to be implicated in the regulation of bone turnover; therefore, SERMs may be useful, alone or in combination with other antiresorbtive or proosteogenic agents, in the treatment or prevention of bone disorders according to appropriate therapeutic sequences or regimens.

In addition, estrogens are involved in the regulation of the balance between $Th_1$ and $Th_2$ predominant immune functions and may therefore be useful in the treatment or prevention of gender-dependent auto-immune diseases such as lupus, multiple sclerosis, rheumatoid arthritis.

Another aspect of the invention thus consists in a method for the treatment or prevention of the above-mentioned diseases or disorders, wherein a therapeutically effective amount of a compound of formula (I) or a pharmaceutically acceptable salt thereof is administered to a patient or animal in need of such treatment or prevention. Co-administration with one or more active substances suitable for the treatment or prevention of said diseases or disorders is also encompassed by the present invention.

The compounds of the invention can in particular be used in the following indications:
  treatment of cognitive dysfunction, for instance as neuroprotective, antidepressant or anxiolytic agents.
  treatment of schizophrenia or neurodegenerative diseases such as Alzheimer's disease or Parkinson's disease.
  prevention or treatment of estrogen-dependent disorders, for example hot flushes, osteoporosis, perimenopausal mood, perimenstrual syndromes, vasomotor related syndromes, vaginal atrophy or dryness, sexual dysfunction such as libido decrease, urinary incontinence, pruritus, local infections of the genital tract. In this case, said compounds can be combined with a sexual endocrine therapeutic agent.
  control or management of reproductive functions, such as male or female fertility, pregnancy, abortion, contraception, delivery, or estrogen-related skin diseases. In this case, said compounds can be combined with a LH-RH agonist or antagonist, an estroprogestative contraceptive, a progestin, an antiprogestin or a prostaglandin.
  prevention or treatment of benign or malignant diseases of the breast, the uterus or the ovary, or of polycystic ovary syndrome. In this case, said compounds can be combined with an antiestrogen, a progestin or a LH-RH agonist or antagonist.
  prevention or treatment of benign or malignant diseases of the prostate or the testis. In this case, said compounds can be combined with an antiandrogen, a progestin, a lyase inhibitor or a LH-RH agonist. If necessary, the compounds of the invention can also be combined with a radiotherapeutic agent; a chemotherapeutic agent such as a nitrogenated mustard analogue like cyclophosphamide, melphalan, iphosphamide, or trophosphamide; an ethylenimine like thiotepa; a nitrosourea like carmustine; a lysed agent like temozolomide or dacarbazine; an antimetabolite of folic acid like methotrexate or raltitrexed; a purine analogue like thioguanine, cladribine or fludarabine; a pyrimidine analogue like fluorouracil, tegafur or gemcitabine; an alkaloid of vinca or analogue like vinblastine, vincristine or vinorelbine; a podophyllotoxin derivative like etoposide, taxanes, docetaxel or paclitaxel; an anthracycline or analogue like doxorubicin, epirubicin, idarubicin or mitoxantrone; a cytotoxic antibiotic like bleomycin or mitomycin; a platinum compound like cisplatin, carboplatin or oxaliplatin; a monoclonal antibody like rituximab; an antineoplastic agent like pentostatin, miltefosine, estramustine, topotecan, irinotecan or bicalutamide; or with a prostaglandin inhibitor (COX 2/COX 1 inhibitor).
  prevention or treatment of irritable bowel syndrome, Crohn's disease, ulcerative proctitis, colitis or arthritis.
  prevention or treatment of cardiovascular diseases, atherosclerosis, hypertension, restenosis (e.g. for lowering cholesterol, triglycerides, Lp(a), or LDL levels, or modulating HDL level).

As used herein, the term "combined" or "combination" refers to any protocol for the co-administration of a compound of formula (I) and one or more other pharmaceutical substances, irrespective of the nature of the time of administration and the variation of dose over time of any of the substances. The co-administration can for example be parallel, sequential or over an extended period of time.

The compounds of formula (I) or their pharmaceutically acceptable salts may be administered, for example, orally, topically, parenterally, in dosage unit formulations containing conventional non-toxic pharmaceutically acceptable carriers, adjuvants and/or vehicles. These dosage forms are given as examples, but other dosage forms may be developed by those skilled in the art of formulation, for the administration of the compounds of formula (I). The term parenteral as used herein includes subcutaneous injections, intravenous, intramuscular or intrasternal injections or infusion techniques. In addition to the treatment of warm-blooded animals such as mice, rats, horses, cattle sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256, 108, 4,166,452 and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active ingredient in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents such as a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those mentioned above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents include naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Acceptable vehicles and solvents that may be employed include water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage levels of the order of from about 0.001 mg to about 10 mg/kg of body weight per day are useful in the treatment or prevention of the above-mentioned diseases or disorders, or alternatively about 0.1 mg to about 100 mg per patient per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The indazole derivatives of formula (I) can be prepared according to general schemes Ia, Ib, Ic.

Scheme Ia

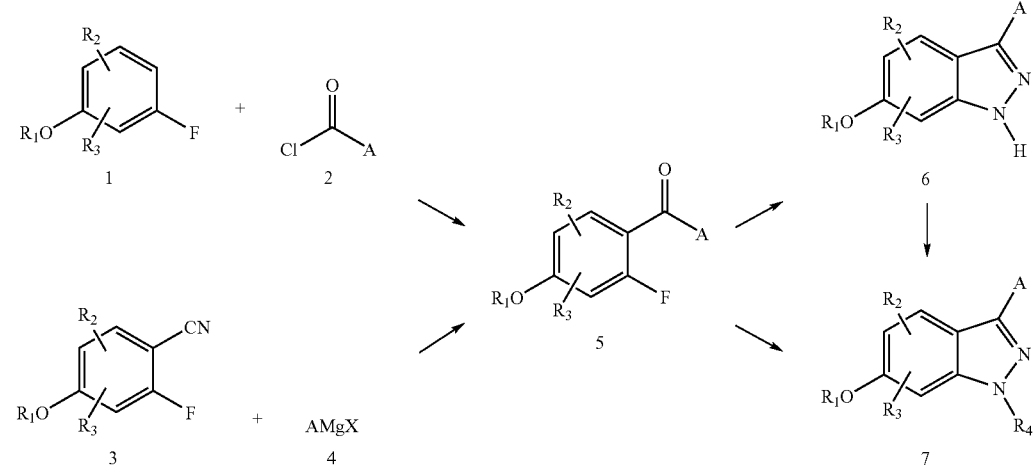

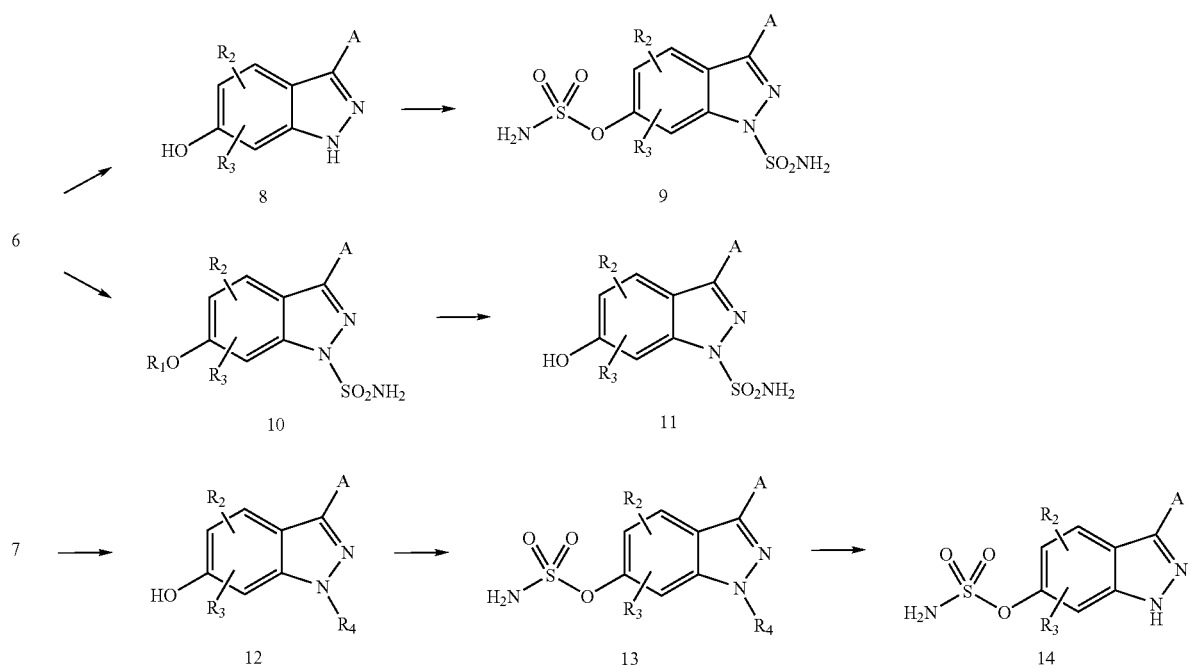

(R₄ = alkyl, X = halogen)

According to scheme Ia fluoroanisole derivative (1) is reacted with a suitable acid chloride of formula (2) by Friedel-Craft reaction following the procedure described by K L Kees (J Med Chem, 29, 11, 1986, 2329-2334) to give ketone (5). This ketone (5) can also be obtained by condensation of alkylmagnesium (4) on fluorobenzonitrile derivative (3) according to H. Shaffer (J Am Chem Soc, 1939, 61, 2175). The ketone (5) is then refluxed in EtOH in the presence of substituted hydrazine or in hydrazine hydrate to afford respectively the cyclised indazoles (6) and (7). The compound (7) can also be prepared by selective N-alkylation of indazole (6) using the conditions described by U. Lerch and J. König (Synthesis, 1983, 2, 157-8) or the conditions described by J Chung and all (Tetrahedron Letters, 1992, 33, 4717-20).

Demethylation of compounds (6) and (7) (if R₁ is methyl) with either tribromoborane using the conditions described by J. F. W. McOmie (Tetrahedron, 1968, 24, 2289-92) or HBr/AcOH or pyridinium hydrochloride or debenzylation of compounds (6) and (7) (if R₁ is benzyl) with Pd/C with or without PtO₂ using the conditions described by W. H. Hartung (Org. React., VII, 1953, 263) give respectively the hydroxy indazole compounds (8) and (12). Indazole (6) can be directly N-sulfamoylated to give (10) by treatment with sodium hydride and sulfamoyl chloride as described by P. Nussbaumer (J. Med. Chem., 2002, 45, 4310-20), or by reaction with sulfamoyl chloride in dimethylacetamide (DMAc) as described by O. Makoto (Tetrahedron Letters, 2000, 41, 7047-51), then deprotected to obtain sulfamate compound (II). Deprotected indazole (8) can be disulfamoylated to give (9). In the same way, indazole (12) can be reacted with sulfamoyl chloride to give O-sulfamate compound (13) and then deprotected to give (14).

Scheme Ib

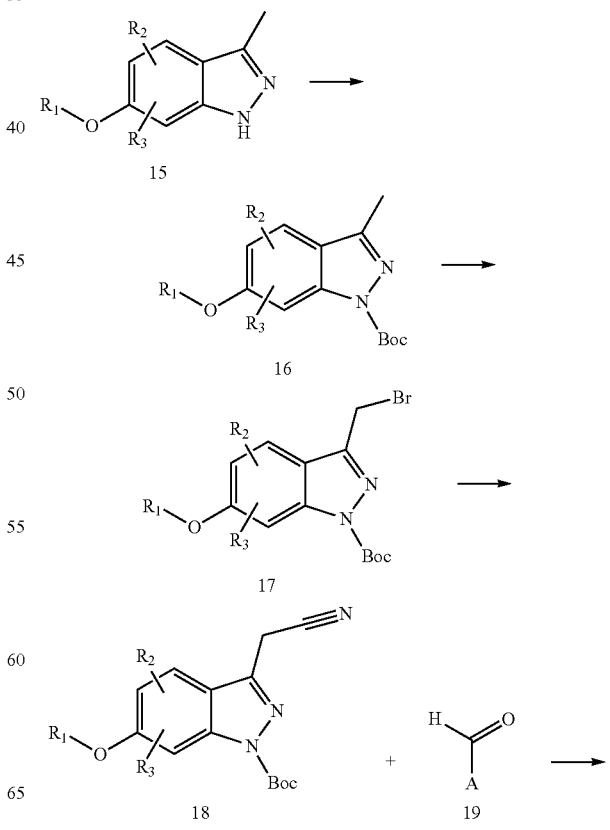

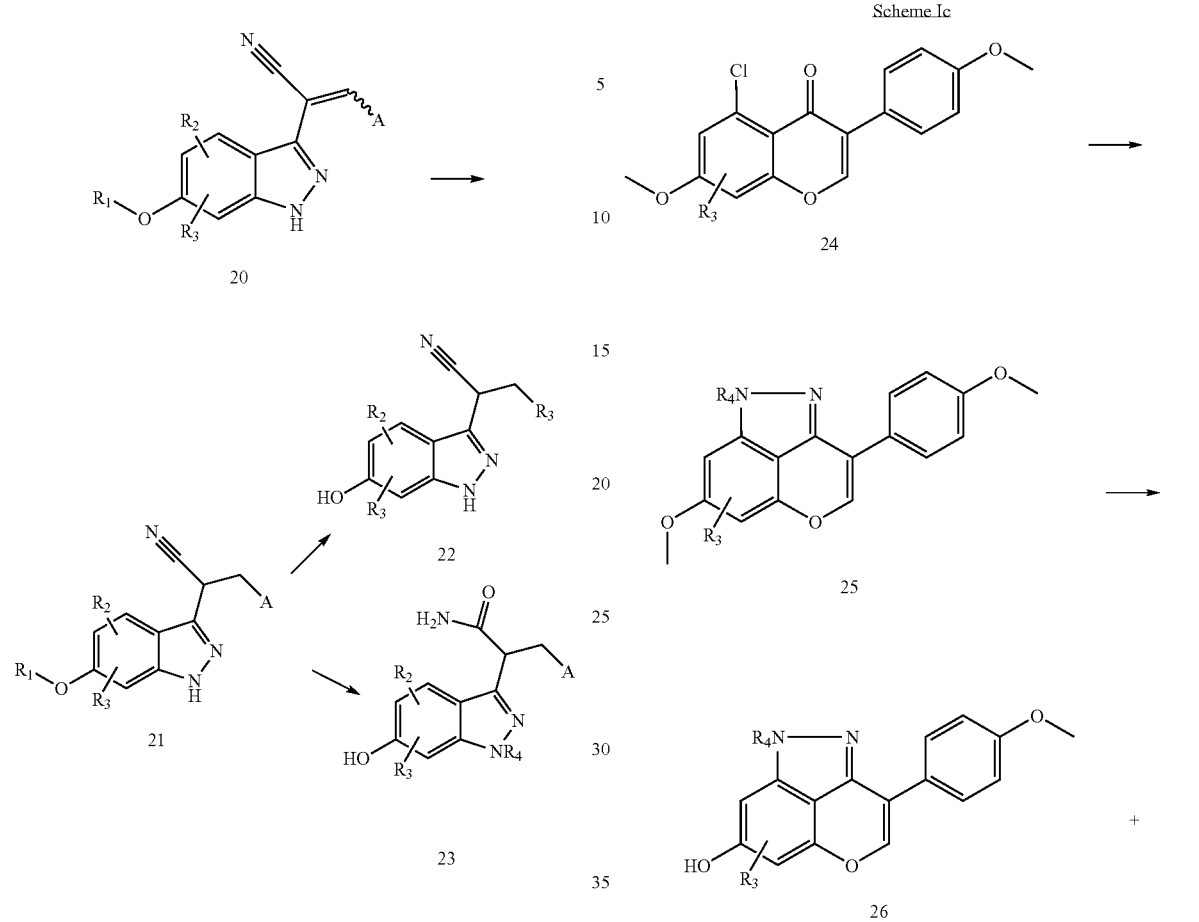
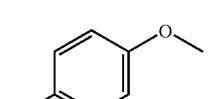
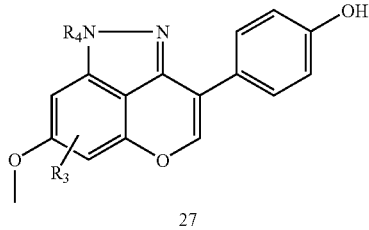

According to scheme Ib, the 3-methyl indazole compound (15) prepared using the conditions described by F. Dennler (Tetrahedron, 22, 1966, 3131) was reacted with $BOC_2O$, TEA and DMAP (T. Ishizuki, Tetrahedron Lett., 28, 1987, 4185) to afford (16). Compound (16) was brominated by Wohl-Ziegler reaction in presence of NBS and benzoyl peroxide following B. R. Henke (J. Med. Chem., 1997, 40, 17, 2706-2725) to give (17). Compound (18) was obtained by reaction of (17) with KCN using the conditions described by Ainsworth (J. Am. Chem. Soc., 1957, 79, 5242-5243). (18) was then reacted with aldehyde (19) in NaH/DMF or KOH/EtOH to give (20) following the procedure described by M. J. Meyers (J. Med. Chem., 44, 24, 2001, 4230) (BOC deprotection was performed during this reaction). Compound (20) was then reacted with $NaBH_4$ in EtOH to give (21). Demethylation of compound (21) (if $R_1$ is methyl) with either tribromoborane using the conditions described by J. F. W. McOmie (Tetrahedron, 1968, 24, 2289-92) or HBr/AcOH or pyridinium hydrochloride or debenzylation of compound (21) (if $R_1$ is benzyl) with Pd/C with or without $PtO_2$ using the conditions described by W. H. Hartung (Org. React., VII, 1953, 263) gave nitrile compound (22). Demethylation with HBr/AcOH gave amide compound (23).

According to scheme Ic, compound (24), prepared using the conditions described by M. Kitagawa (Chem. Pharm. Bull., 39, 10, 1991, 2681), was reacted with hydrazine hydrate or alkyl or aryl hydrazine under reflux to give compound (25). Compound (25) was demethylated in the presence of $BBr_3$ in $CH_2Cl_2$ using the conditions described by McOmie J. F. W (Tetrahedron, 1968, 24, 2289-92) to give compounds (26) and (27).

The benzisoxazole derivatives of formula (I) can be prepared according to general schemes IIa, IIb, IIc.

Scheme IIa

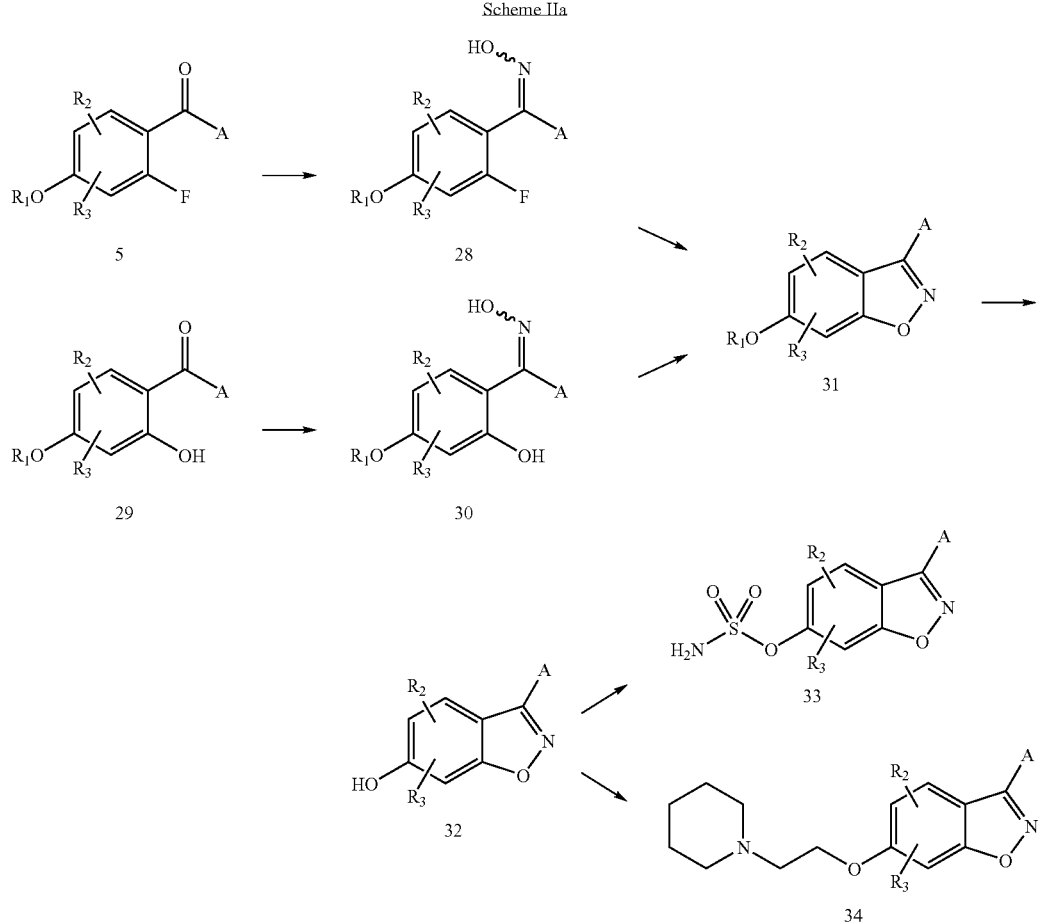

According to scheme IIa, the already described ketone (5) or ketone (29) obtained by Friedel-Craft procedure described by K L Kees (J Med Chem, 29, 11, 1986, 2329-2334) are refluxed in hydroxylamine hydrochloride using the conditions described by Y. Yamanaka (Pestic. Sci., 1998, 54, 3, 223-229) to afford respectively uncyclised oxime (28) and (30). Compound (28) is then cyclised in refluxing NaOH/ EtOH solution and compound (30) is cyclised using an intramolecular Mitsunobu reaction (Synthesis, 1981, 1) to afford the corresponding benzisoxazole (31).

Demethylation of compound (31) (if $R_1$ is methyl) with either tribromoborane using the conditions described by J. F. W. McOmie (Tetrahedron, 1968, 24, 2289-92) or HBr/AcOH or pyridinium hydrochloride or debenzylation of compounds (31) (if $R_1$ is benzyl) with Pd/C using conditions described by A. M. Felix (J. Org. Chem., 43, 1978, 4194) give the hydroxy benzisoxazole compound (32). This compound (32) can be transformed into the corresponding sulfamate (33) by treatment with sodium hydride and sulfamoyl chloride (P. Nussbaumer., J. Med. Chem., 2002, 45, 4310-20), or by reaction with sulfamoyl chloride in dimethylacetamide (DMAc) (O. Makoto, Tetrahedron letters, 2000, 41, 7047-51). Compound (32) can also be transformed into ether compound (34) by reaction with 1-(2-chloroethyl)piperidine using conditions described by M. R. Tremblay (Bioorg. Med. Chem., 1999, 7, 6, 1013-1024).

Scheme IIb

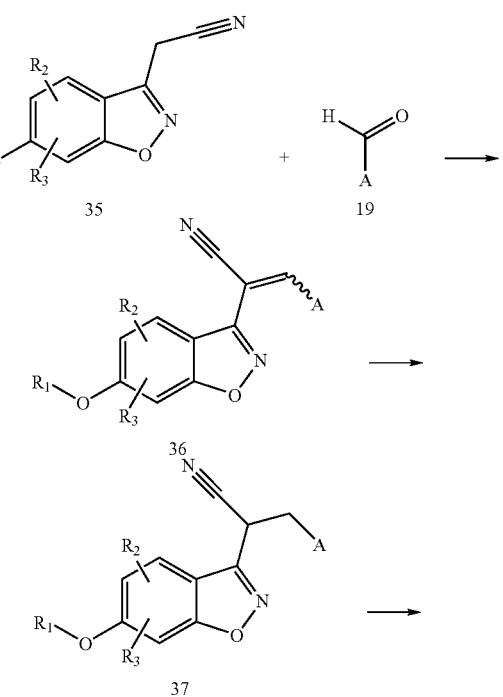

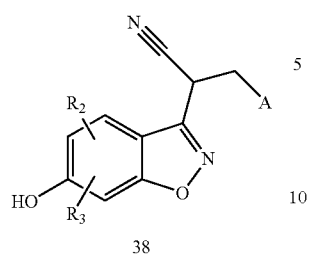

According to scheme IIb the benzisoxazole (35) prepared using the conditions described by H. Uno (Chem. Pharm. Bull., 24, 1976, 632) was reacted with aldehyde (19) in NaH/DMF or KOH/EtOH to give (36). Compound (36) was reacted with NaBH$_4$ in EtOH to give (37).

Demethylation of compound (37) with either tribromoborane using the conditions described by J. F. W. McOmie (Tetrahedron, 1968, 24, 2289-92) or HBr/AcOH or pyridinium hydrochloride gave the hydroxy benzisoxazole compound (38).

Scheme IIc

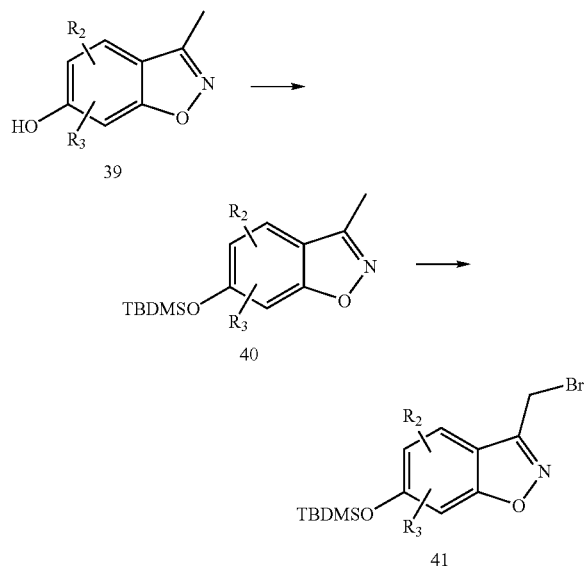

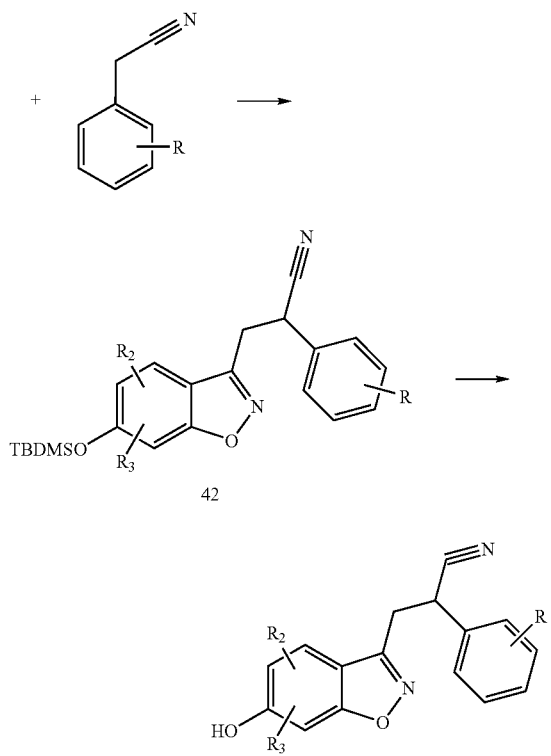

According to scheme IIc the benzisoxazole (39) prepared using the conditions described by M. A. Elkasaby (Indian J. Chem. Sect B, 1980, 19, 571) was protected with tert-butyldimethylsilylchloride in imidazole/DMF (P. M. Kendall, J. Org. Chem., 44, 1979, 1421) and the compound (40) obtained was brominated in the presence of NBS and benzoyl peroxide to give (41). Compound (41) was reacted with LDA and substituted phenylacetonitrile to give (42) using the procedure described by E. Teodori (Bioorg. Med. Chem., 7, 9, 1999, 1873-1880). Deprotection of the hydroxyl group in presence of nBu$_4$F using the conditions described by E. J. Corey (J. Am. Chem. Soc., 94, 1972, 6190) gave compound (43).

The benzisothiazole derivatives of formula (I) can be prepared according to general scheme III.

Scheme III

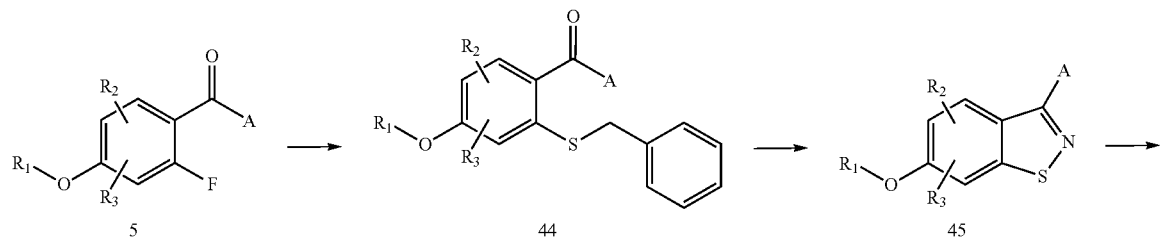

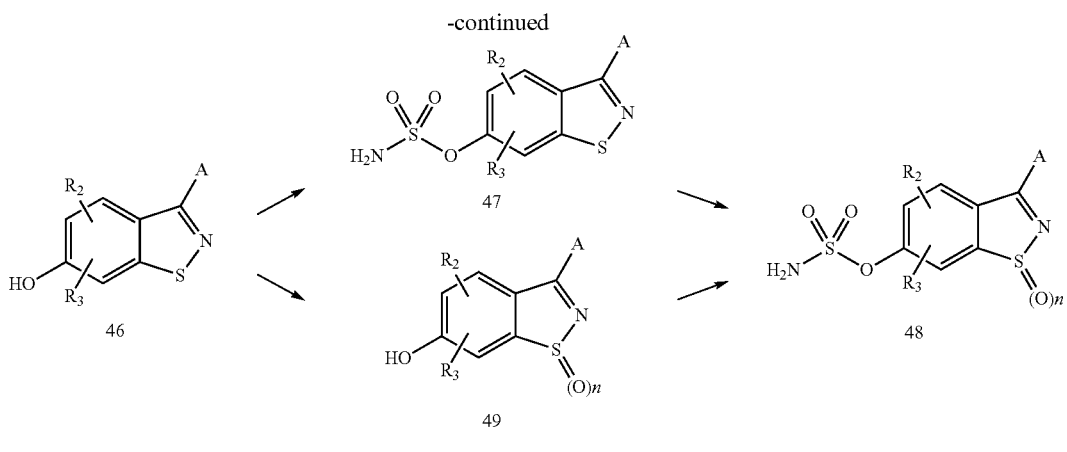

(n = 1, 2)

According to scheme III, ketone (5) was reacted with phenylmethanethiol to give (44). The obtained compound (44) was refluxed in sulfuryl chloride followed by ammoniac treatment to afford cyclised benzisothiazole (45) according to the procedure described by D. M. Fink (Tetrahedron Letters, 1993, 34, 41, 6525-6528). Demethylation of compounds (45) with either tribromoborane using the conditions described by J. F. W McOmie (Tetrahedron, 1968, 24, 2289-92) or HBr/AcOH or pyridinium hydrochloride gave the hydroxy benzisothiazole compounds (46). These compounds (46) can be transformed into the corresponding sulfamates (47) by treatment with sodium hydride and sulfamoyl chloride (P. Nussbaumer, J. Med. Chem., 2002, 45, 4310-20), or by reaction with sulfamoyl chloride in dimethylacetamide (DMAc) (O. Makoto. Tetrahedron letters, 2000, 41, 7047-51).

Oxidation of these compounds (46) and (47) by hydrogen peroxide in trifluoroacetic acid, following the conditions described by S. Grivas and E. Ronne (Acta Chemica Scandinavia, 1995, 49, 225-229), gave respectively the mono and/or dioxidised benzisothiazoles (49) and (48). Compound (49) can be sulfamoylated to give (48).

General schemes I, II and III illustrate the synthesis of compounds (I) in which the substituent $R_1O$ is in position 6- of the heterocyclic ring. It will however be appreciated that compounds (I) where the substituent $R_1O$ is in position 4-, 5- or 7- of the heterocyclic ring can be prepared using the procedures described above.

The following examples are intended to illustrate and not to limit the scope of the invention.

Preparation of Acetophenones (5)

Example 1

4-benzyloxy-2-fluorobenzonitrile

To a mixture of 2-fluoro-4-hydroxy-benzonitrile (98 g, 0.68 mol) and $K_2CO_3$ (94 g, 0.68 mol) in acetonitrile was added benzyl chloride (86.6 g, 0.68 mol). The mixture was stirred overnight at room temperature and the reaction followed by TLC (toluene/AcOEt 8/2). The mixture was filtered, concentrated under vacuum and crystallized from pentane to give 147 g of solid (95%).

$^1$H-NMR (DMSO $d_6$): 5.25 (s, 2H), 7.05 (dd, 1H), 7.25 (dd, 1H), 7.30-7.60 (m, 5H), 7.75 (t, 1H).

Using the same procedure but replacing 2-fluoro-4-hydroxy-benzonitrile by:
cycloheptyl (2-fluoro-4-hydroxyphenyl)methanone
1-adamantyl (2-fluoro-4-hydroxyphenyl)methanone
the following compounds were respectively obtained:

Example 2 cycloheptyl (4-benzyloxy-2-fluorophenyl)methanone (71%).
$^1$H-RMN(CDCl$_3$): 1.10-2.00 (m, 12H), 3.50 (m, 1H), 5.17 (s, 2H), 6.85 (dt, 1H), 7.20 (dd, 1H), 7.30-7.60 (m, 6H).

Example 3

1-adamantyl (4-benzyloxy-2-fluorophenyl)methanone (38%)
$^1$H-NMR (DMSO $d_6$): 1.30-2.30 (m, 15H), 5.20 (s, 2H), 6.85 (dt, 1H), 7.12 (dd, 1H), 7.20-7.60 (m, 6H).

Example 4 cyclopentyl (4-benzyloxy-2-fluorophenyl)methanone

A suspension of magnesium (19 g, 0.79 mol) and iodine (catalytic amount) in THF (20 ml) was refluxed under $N_2$. A solution of cyclopentylbromide (110 g, 0.738 mol) in THF (400 ml) was added slowly. The mixture was refluxed until all the magnesium was consumed, then cooled to 30° C. and added to a solution of 4-benzyloxy-2-fluorobenzonitrile (129 g, 0.56 mol) in THF (600 ml). The reaction was stirred at 50° C. overnight then quenched by aqueous NH$_4$Cl and ice, extracted with ethyl acetate, and washed with brine. The mixture was dried over Na$_2$SO$_4$, filtered and concentrated under vacuum. Purification by flash chromatography (heptane/EtOAc 9/1) gave 60 g of product (35%, as solid).

$^1$H-NMR (DMSO $d_6$): 1.40-2.00 (m, 8H), 3.58 (m, 1H), 5.20 (s, 2H), 6.85-7.20 (m, 2H), 7.25-7.55 (m, 5H), 7.80 (t, 1H).

Using the same procedure but replacing cyclopentylbromide by cyclohexylchloride, the following compound was obtained:

Example 5 cyclohexyl (4-benzyloxy-2-fluorophenyl)methanone (35%). mp 78° C.
$^1$H-NMR (DMSO d$_6$): 1.00 to 2.00 (m, 10H), 3.05 (m, 1H), 5.20 (s, 2H), 6.90-7.10 (m, 2H), 7.20-7.60 (m, 5H), 7.75 (t, 1H).

Example 6

1-adamantyl (2-fluoro-4-hydroxyphenyl)methanone

To a mixture of AlCl$_3$ (45 g, 0.337 mol) in 1,2-dichloroethane (DCE, 250 ml) at 0° C. was added 1-adamantyl carbonyl chloride (36.6 g, 0.228 mol) in DCE (150 ml). 3-fluorophenol (21 g, 0.183 mol) in DCE (100 ml) was added slowly at 0° C. The reaction was followed by TLC (heptane/toluene 50/50). The mixture was poured onto HCl 2N, extracted with AcOEt, washed with NaHCO$_3$ and brine, dried over Na$_2$SO$_4$, filtered and concentrated under vacuum. Purification by flash chromatography (heptane/toluene 8/2) gave 27 g of 1-adamantyl (2-fluoro-4-hydroxyphenyl)methanone (48% as solid).
$^1$H-NMR (DMSO, d$_6$): 1.30 (m, 15H), 5.97 (s, 1H), 6.70 (d, 1H), 6.94 (dd, 1H), 7.64 (d, 1H).

Using the same procedure but replacing 1-adamantyl carbonyl chloride by cycloheptane carbonyl chloride, the following compound was obtained:

Example 7 cycloheptyl (2-fluoro-4-hydroxyphenyl)methanone (60%).
$^1$H-RMN (CDCl$_3$): 1.20-2.00 (m, 12H), 3.58 (m, 1H), 6.70-6.90 (m, 2H), 7.90-8.10 (m, 1H), 12.45 (s, 1H).

Using the same procedure but replacing 1-adamantyl carbonyl chloride by cycloheptane carbonyl chloride and 3-fluorophenol by 3-fluoroanisole, the following compound was obtained:

Example 8 cycloheptyl (4-methoxy-2-fluorophenyl)methanone (45%).
$^1$H-NMR (CDCl$_3$): 1.40-2.00 (m, 12H), 1.9 (3, 2H), 3.25 (m, 1H), 3.80 (s, 3H), 6.50 (dd, 1H), 6.65 (dd, 1H), 7.75 (t, 1H).

Using the same procedure but replacing 3-fluorophenol by:
3-fluoroanisole
3,5-dimethoxy-chlorobenzene
the following compounds were respectively obtained:

Example 9

1-adamantyl (4-methoxy-2-fluorophenyl)methanone (15%).
$^1$H-NMR (CDCl$_3$): 1.50-2.30 (m, 15H), 3.85 (s, 3H), 6.60 (2d, 1H), 6.70 (2d, 1H), 7.70 (t, 1H).

Example 10

1-adamantyl (2-chloro-4,6-dimethoxyphenyl)methanone (22%).
$^1$H-NMR (CDCl$_3$, d$_1$): 1.60-2.10 (m, 15H), 3.75 (s, 3H), 3.80 (s, 3H), 6.35 (s, 1H), 6.50 (s, 1H).

Using the same procedure but replacing 3-fluorophenol by 3,4-dimethoxy-fluorobenzene and 1-adamantyl carbonyl chloride by cyclohexane carbonyl chloride, the following compound was obtained:

Example 11 cyclohexyl (2-fluoro-4-hydroxy-5-methoxyphenyl)methanone $^1$H-NMR (DMSO, d$_6$): 1.00-2.00 (m, 10H), 3.05 (m, 1H), 3.80 (s, 3H), 6.65 (d, 1H), 7.23 (d, 1H), 10.50 (s, 1H).

Preparation of Indazoles (6), (7), (8) and (12)

Example 12

6-benzyloxy-3-cyclopentyl-1H-indazole

A mixture of cyclopentyl (4-benzyloxy-2-fluorophenyl)methanone (40 g, 0.13 mol) in hydrazine hydrate (50 ml) was refluxed overnight. After cooling to room temperature, the solid was filtered, dissolved in EtOAc, then washed with aqueous NH$_4$Cl and brine. The solution was dried over Na$_2$SO$_4$, filtered and concentrated under vacuum. Purification by flash chromatography (toluene/EtOAc 9/1) gave the expected product (13 g, 45% as solid).
$^1$H-NMR (DMSO d$_6$): 1.40-2.20 (m, 8H), 3.34 (m, 1H), 5.13 (s, 2H), 6.75 (dd, 1H), 6.90 (d, 1H), 7.20-7.53 (m, 5H), 7.57 (d, 1H), 9.40 (s, 1H).

Using the same procedure but replacing cyclopentyl (4-benzyloxy-2-fluorophenyl)methanone by:
cyclohexyl (4-benzyloxy-2-fluorophenyl)methanone
cycloheptyl (4-benzyloxy-2-fluorophenyl)methanone
1-adamantyl (4-methoxy-2-fluorophenyl)methanone
cycloheptyl (4-methoxy-2-fluorophenyl)methanone
the following compounds were respectively obtained:

Example 13

6-benzyloxy-3-cyclohexyl-1H-indazole (58%).
$^1$H-RMN (CDCl$_3$): 1.10-2.10 (m, 10H), 2.95 (m, 1H), 5.15 (s, 2H), 6.75 (dd, 1H), 6.90 (d, 1H), 7.20-7.55 (m, 5H), 7.65 (d, 1H), 12.32 (s, 1H).

Example 14

6-benzyloxy-3-cycloheptyl-1H-indazole (85%).
$^1$H-RMN (CDCl$_3$): 1.20-2.10 (m, 12H), 2.55 (m, 1H), 5.07 (s, 2H), 6.45 (dd, 1H), 6.55 (d, 1H), 6.95 (d, 1H), 7.20-7.50 (m, 5H).

Example 15

3-(1-adamantyl)-6-methoxy-1H-indazole (30%).
$^1$H-NMR (CDCl$_3$): 1.50-2.70 (m, 15H), 3.85 (s, 3H), 6.78 (dd, 1H), 6.88 (d, 1H), 7.57 (d, 1H).

Example 16

3-cycloheptyl-6-methoxy-1H-indazole (45%).
$^1$H-NMR (CDCl$_3$): 1.40-2.30 (m, 12H), 3.22 (m, 1H), 3.83 (s, 3H), 6.35 (s, 1H), 6.65-6.90 (m, 2H), 7.58 (d, 1H).

Using the same procedure but replacing hydrazine hydrate by 1-(4-benzyloxyphenyl)hydrazine (prepared following K. J. Duffy, J Med Chem 2001, 44, 22, 3730-3745), the following compound was obtained:

Example 17

6-benzyloxy-3-cyclopentyl-1-(4-benzyloxyphenyl)-1H-indazole (66%).
$^1$H-RMN (DMSO d$_6$): 1.15-2.05 (m, 10H), 2.95 (dt, 1H), 3.88 (s, 3H), 5.15 (s, 2H), 6.75 (dd, 1H), 7.12 (d, 1H), 7.25-7.58 (m, 5H), 7.65 (d, 1H).

Using the same procedure but replacing cyclopentyl (4-benzyloxy-2-fluorophenyl)methanone by cyclohexyl (4-benzyloxy-2-fluorophenyl)methanone and hydrazine hydrate by methylhydrazine or benzylhydrazine, the following compound were respectively obtained:

Example 18

6-benzyloxy-3-cyclohexyl-1-methyl-1H-indazole (66%).
$^1$H-RMN (DMSO d$_6$): 1.15-2.05 (m, 10H), 2.95 (dt, 1H), 3.88 (s, 3H), 5.15 (s, 2H), 6.75 (dd, 1H), 7.12 (d, 1H), 7.25-7.58 (m, 5H), 7.65 (d, 1H).

Example 19

1-benzyl-6-benzyloxy-3-cyclohexyl-1H-indazole (76%).
$^1$H-RMN (DMSO d$_6$): 1.15-2.05 (m, 10H), 2.95 (dt, 1H), 5.10 (s, 2H), 5.15 (s, 2H), 6.75 (dd, 1H), 7.12 (d, 1H), 7.15-7.65 (m, 10H), 7.65 (d, 1H).

Example 20

Tertio-butyl-6-benzyloxy-3-cyclohexyl-1H-indazole-1-carboxylate

At 0° C. di-tert-butyldicarbonate (36.38 g, 0.166 mol) in acetonitrile (340 ml) was added on a mixture of 6-benzyloxy-3-cyclohexyl-1H-indazole (42.50 g, 0.138 mol), TEA (22 ml, 0.152 mol), acetonitrile (460 ml) and DMAP (3.40 g, 0.027 mol).

The mixture was stirred at room temperature overnight, then concentrated under vacuum, diluted with ethyl acetate and washed with water acidified with HCl 2N to pH 2. The mixture was dried over Na$_2$SO$_4$, filtered and diluted in diisopropyl ether, the expected product crystallized (44.50 g, yield 79%).
$^1$H-NMR (DMSO d$_6$): 1.15-2.05 (m, 19H), 3.00 (m, 1H), 5.19 (s, 2H), 7.03 (dd, 1H), 7.25-7.45 (m, 5H), 7.69 (d, 1H), 7.78 (d, 2H).

Example 21

6-benzyloxy-3-cyclopentyl-1-(2-piperidin-1-yl-ethyl)-1H-indazole 6-benzyloxy-3-cyclopentyl-1H-indazole was heated for 1 hour with NaOH (1.64 g, 41 mmol) and 1-(2-chloroethyl) piperidine in EtOH (60 ml) at 40° C. The reaction was followed by TLC (toluene/dioxane: 7/3), and when completed, the mixture was cooled to room temperature. The mixture was quenched by NH$_4$Cl, extracted with AcOEt, dried over Na$_2$SO$_4$, filtered and concentrated under vacuum. Purification by flash chromatography (toluene/1,4-dioxane 7/3) gave the expected product (600 mg, 8% as solid).
$^1$H-RMN (DMSO d$_6$): 1.40-2.40 (m, 14H), 2.50-2.80 (m, 2H), 3.10-3.60 (m, 5H), 4.30 (t, 2H), 5.15 (s, 2H), 6.70 (dd, 1H), 7.10 (d, 1H), 7.40 (m, 5H), 7.60 (d, 1H).

Using the same procedure but replacing 1-(2-chloroethyl) piperidine by 4-bromobenzylbromide, the following compound was obtained:

Example 22

6-benzyloxy-1-(4-bromobenzyl)-3-cyclopentyl-1H-indazole $^1$H-RMN (DMSO d$_6$): 1.50-2.20 (m, 8H), 3.38 (m, 1H), 5.15 (s, 2H), 5.50 (s, 2H), 6.78 (dd, 1H), 7.05-7.55 (m, 10H), 7.60 (d, 1H).

Example 23

3-cyclopentyl-1H-indazol-6-ol

A mixture of 6-benzyloxy-3-cyclopentyl-1H-indazole (13 g, 0.102 mol), Pd/C (5%, 0.65 g) and PtO$_2$ (catalytic amount) in ethanol (130 ml) was stirred at room temperature under hydrogen. The reaction was followed by TLC (heptane/EtOAc 50/50). When completed, the mixture was filtered on Celite® and concentrated under vacuum. Crystallization from CH$_2$Cl$_2$/pentane gave 7.2 g of white crystals (85%). mp 175° C.
$^1$H-NMR (DMSO, d$_6$): 1.40-2.20 (m, 8H), 3.35 (m, 1H), 6.55 (dd, 1H), 6.68 (d, 1H), 7.50 (d, 1H), 9.45 (s, 1H), 12.05 (s, 1H).

Using the same procedure but replacing 6-benzyloxy-3-cyclopentyl-1H-indazole by:

6-benzyloxy-3-cyclohexyl-1H-indazole 6-benzyloxy-3-cyclohexyl-1-methyl-1H-indazole 6-benzyloxy-3-cyclopentyl-1-(4-benzyloxyphenyl)-1H-indazole 6-benzyloxy-3-cyclopentyl-1-(2-piperidin-1-yl-ethyl)-1H-indazole 6-benzyloxy-1-(4-bromobenzyl)-3-cyclopentyl-1H-indazole 1-benzyl-6-benzyloxy-3-cyclopentyl-1H-indazole Tertio-butyl-6-benzyloxy-3-cyclohexyl-1H-indazole-1-carboxylate the following compounds were respectively obtained:

Example 24

3-cyclohexyl-1H-indazol-6-ol (85%). mp 147° C.
$^1$H-RMN (DMSO d$_6$): 1.10-2.10 (m, 10H), 2.90 (m, 1H), 6.55 (dd, 1H), 6.65 (s, 1H), 7.50 (d, 1H), 9.45 (s, 1H), 12.05 (s, 1H).

Example 25

3-cyclohexyl-1-methyl-1H-indazol-6-ol (75%). mp 205° C.
$^1$H-RMN (DMSO d$_6$): 1.20-2.00 (m, 10H), 2.92 (dt, 1H), 3.80 (s, 3H), 6.60 (dd, 1H), 6.68 (d, 1H), 7.55 (d, 1H), 9.58 (s, 1H).

Example 26

3-cyclopentyl-1-(4-hydroxyphenyl)-1H-indazol-6-ol (54%). mp 178° C.
$^1$H-RMN (DMSO d$_6$): 1.50-2.20 (m, 8H), 3.40 (t, 1H), 6.68 (dd, 1H), 6.83 (d, 1H), 6.90 (d, 2H), 7.38 (d, 2H), 7.59 (d, 1H), 9.60 (s, 1H), 9.68 (s, 1H).

Example 27

3-cyclopentyl-1-(2-piperidin-1-yl-ethyl)-1H-indazol-6-ol, hydrochloride (90%). mp 120° C.
$^1$H-NMR (DMSO d$_6$): 1.15-2.30 (m, 14H), 2.90 (m, 2H), 3.20-3.60 (m, 5H), 4.68 (t, 2H), 6.70 (dd, 1H), 6.88 (d, 1H), 7.52 (d, 1H), 10.80 (s, 1H).

Example 28

1-(4-bromobenzyl)-3-cyclopentyl-1H-indazol-6-ol (90%). mp 147° C.
$^1$H-RMN (DMSO d$_6$): 1.45-2.30 (m, 8H), 3.35 (m, 1H), 5.40 (s, 2H), 6.60 (d, 1H), 7.00-7.40 (m, 4H), 7.50 (d, 1H), 7.70 (s, 1H).

Example 29

1-benzyl-3-cyclohexyl-1H-indazol-6-ol (40%) mp 154° C.
$^1$H-NMR (CDCl$_3$): 1.10-2.40 (m, 10H), 3.03 (m, 1H), 5.40 (s, 2H), 5.70 (s, 1H), 6.53 (d, 1H), 6.76 (dd, 1H), 7.00-7.35 (m, 5H), 7.60 (d, 1H).

Example 30

Tertio-butyl-3-cyclohexyl-6-hydroxy-1H-indazol-1-carboxylate (87%) mp 124° C.
$^1$H-NMR (DMSO d$_6$): 1.20-2.05 (m, 19H), 2.95 (m, 1H), 6.80 (dd, 1H), 7.40 (d, 1H), 7.65 (d, 1H).

Example 31

3-(1-adamantyl)-1H-indazol-6-ol, hydrochloride

A mixture of 3-(1-adamantyl)-6-methoxy-1H-indazole (210 mg, 0.75 mol) in 40% HBr in acetic acid (10 ml) was heated overnight at 70° C. The mixture was poured onto ice and neutralised with a solution of NaHCO$_3$, then extracted with AcOEt, dried over Na$_2$SO$_4$, filtered and concentrated under vacuum. Purification by flash chromatography (heptane/EtOAc 50/50) gave 200 mg of product. The solid was crystallised as HCl salt from Et$_2$O. The crystals were filtered, washed with ether, and dried to give 160 mg of salt (80%). mp 140° C.
$^1$H-NMR (DMSO d$_6$): 1.00-2.60 (m, 15H), 6.65 (d, 1H), 6.75 (s, 1H), 7.55 (d, 1H).

Using the same procedure but replacing 3-(1-adamantyl)-6-methoxy-1H-indazole by 3-cycloheptyl-6-methoxy-1H-indazole, the following compound was obtained:

Example 32

3-cycloheptyl-1H-indazol-6-ol, hydrochloride (60%). mp 95° C.
$^1$H-NMR (DMSO d$_6$): 1.20-2.00 (m, 12H), 3.1 (m, 1H), 6.62 (d, 1H), 6.64 (s, 1H), 7.60 (d, 1H).

Preparation of 1H-indazole sulfonamides (9), (10), (11), (13) and (14)

Example 33

6-benzyloxy-3-cycloheptyl-1H-indazole-1-sulfonamide

Sulfamoyl chloride (2.9 g, 25 mmol) was added to a solution of 6-benzyloxy-3-cycloheptyl-1H-indazole (6) (4 g, 1.75 mmol) in N,N-dimethylacetamide (40 ml) at 0° C. The mixture was stirred for 3 h at 0° C. After extraction with EtOAc, the organic layer was washed with NH$_4$Cl solution and brine. It was dried over Na$_2$SO$_4$, filtered and concentrated under vacuum. Purification by flash chromatography followed by crystallisation from EtOH gave 1.2 g of yellow crystals (24%).
$^1$H-NMR (DMSO d$_6$): 1.20-2.00 (m, 12H), 2.58 (m, 1H), 5.05 (s, 2H), 6.65-7.00 (m, 1H), 7.20-7.50 (m, 6H), 7.92 (s, 1H), 8.55 (s, 2H).

Using the same procedure but replacing 6-benzyloxy-3-cycloheptyl-1H-indazole by:
6-benzyloxy-3-cyclohexyl-1H-indazole
3-cyclohexyl-1H-indazol-6-ol
3-cyclohexyl-1-methyl-1H-indazol-6-ol
1-benzyl-3-cyclohexyl-1H-indazol-6-ol
Tertio-butyl-6-benzyloxy-3-cyclohexyl-1H-indazole-1-carboxylate
the following compounds were respectively obtained:

Example 34

6-benzyloxy-3-cyclohexyl-1H-indazole-1-sulfonamide (100%).
$^1$H-NMR (DMSO d$_6$): 1.10 to 2.10 (m, 10H), 3.05 (m, 1H), 5.15 (s, 2H), 7.00 (dd, 1H), 7.25-7.60 (m, 6H), 7.80 (d, 1H), 8.35 (s, 2H).

Example 35

1-(aminosulfonyl)-3-cyclohexyl-1H-indazol-6-yl-sulfamate (40%). mp 213° C.
$^1$H-NMR (DMSO d$_6$): 1.20-2.10 (m, 10H), 3.13 (d, 1H), 7.25 (dd, 1H), 7.80 (d, 1H), 8.00 (d, 1H), 8.10 (s, 2H), 8.50 (s, 2H).

Example 36

3-cyclohexyl-1-methyl-1H-indazole-6-sulfonamide (84%). mp 188° C.

$^1$H-NMR (DMSO $d_6$): 1.20-2.10 (m, 10H), 3.03 (m, 1H), 3.95 (s, 3H), 6.98 (d, 1H), 7.45 (s, 1H), 7.85 (d, 1H), 8.00 (s, 2H).

Example 37

1-benzyl-3-cyclohexyl-1H-indazol-6-yl-sulfamate (85%) mp 188° C.

$^1$H-NMR (DMSO $d_6$): 1.10-2.10 (m, 10H), 3.04 (m, 1H), 5.55 (s, 2H), 7.05 (d, 1H), 7.10 (m, 5H), 5.53 (s, 1H), 7.88 (d, 1H), 8.00 (s, 2H).

Example 38

Tertio-butyl-6-[(aminosulfonyl)oxy]-3-cyclohexyl-1H-indazole-1-carboxylate (46%) mp 128° C.

$^1$H-NMR (DMSO $d_6$): 1.20-2.10 (m, 19H), 3.10 (m, 1H), 7.23 (dd, 1H), 7.90-8.05 (m, 2H), 8.11 (s, 2H).

Using the same procedure as in Example 21 but replacing 6-benzyloxy-3-cyclopentyl-1H-indazole by:
6-benzyloxy-3-cycloheptyl-1H-indazol-1-sulfonamide
6-benzyloxy-3-cyclohexyl-1H-indazol-1-sulfonamide
the following compounds were respectively obtained:

Example 39

3-cycloheptyl-6-hydroxy-1H-indazole-1-sulfonamide mp 155° C.

$^1$H-NMR (DMSO $d_6$): 1.20-2.00 (m, 12H), 2.60 (m, 1H), 6.70 (m, 2H), 6.90 (s, 2H), 7.05 (m, 1H), 7.80 (s, 1H).

Example 40

3-cyclohexyl-6-hydroxy-1H-indazole-1-sulfonamide mp 162° C.

$^1$H-NMR (DMSO $d_6$): 1.10-2.10 (m, 10H), 3.00 (m, 1H), 6.78 (dd, 1H), 7.25 (d, 1H), 7.68 (d, 1H), 8.22 (s, 2H), 10.05 (s, 1H).

Example 41

3-cyclohexyl-1H-indazol-6-yl-sulfamate

A mixture of tertio-butyl-6-[(aminosulfonyl)oxy]-3-cyclohexyl-1H-indazole-1-carboxylate (4.00 g, 10.12 mmol), water (10 ml), dioxan (30 ml) and few drops of HCl concentrated (30%) was stirred overnight and poured into water. The precipitate was collected by filtration to give the expected product. Crystallisation from toluene gave white crystals (1.25 g, 48%)

$^1$H-NMR (DMSO $d_6$): 1.10-2.10 (m, 10H), 3.04 (m, 1H), 6.95 (dd, 1H), 7.35 (d, 1H), 7.83 (d, 1H), 7.96 (s, 2H).

Preparation of 3-bromomethyl-1H-indazoles (16), (17) and (18)

Example 42

1-[(tert-butoxycarbonyl)oxy]-6-methoxy-3-methyl-1H-indazole

Di-tert-butyl-dicarbonate in acetonitrile was mixed at 0° C. with 6-methoxy-3-methyl-1H-indazole (prepared following the procedure described by F. Dennler, *Tetrahedron*, 22, 1966, 3131-3139) (26.27 g, 0.162 mol), acetonitrile (200 ml), triethylamine (25 ml, 0.178 mol), DMAP (3.96 g, 0.0324 mol). The mixture was stirred at room temperature overnight. Acetonitrile was concentrated under vacuum. The mixture was extracted with ethylacetate and acidified at pH=2 with a solution of concentrated HCl, dried over $Na_2SO_4$, filtered and put in diisopropylether. 23.9 g of the expected product were obtained (as solid, 59%).

$^1$H-NMR (DMSO $d_6$): 1.60 (s, 9H), 2.44 (s, 3H), 3.85 (s, 3H), 6.95 (dd, 1H), 7.50 (d, 1H), 7.65 (d, 1H).

Example 43

1-[(tert-butoxycarbonyl)oxy]-6-methoxy-3-bromo-methyl-1H-indazole

1-[(tert-butoxycarbonyl)oxy]-6-methoxy-3-methyl-1H-indazole (25.2 g, 0.096 mol) was dissolved in $CCl_4$ and mixed with benzoyl peroxide (2.33 g, 9.6 mmol). N-bromosuccinimide (NBS, 18.8 g, 0.109 mol) was slowly added to this mixture and heated under reflux overnight. The mixture was cooled at room temperature, filtered on Celite®, the filtrate was concentrated under vacuum and flashed with toluene. 10.5 g of the expected product were obtained (32%, as oil).

$^1$H-NMR (DMSO $d_6$): 1.65 (s, 9H), 3.85 (s, 3H), 4.95 (s, 2H), 7.05 (dd, 1H), 7.55 (s, 1H), 7.80 (d, 1H)

Example 44

{1-[(tert-butoxycarbonyl)oxy]-6-methoxy-1H-indazol-3-yl}acetonitrile

KCN (5.73 g, 88 mmol) in 23 ml of $H_2O$ was added dropwise at 0° C. to 1-[(tert-butoxycarbonyl)oxy]-6-methoxy-3-bromomethyl-1H-indazole (10.5 g, 30.08 mmol) in 80 ml of ethanol and stirred at room temperature for 1 h 30. The mixture was poured into water, and extracted with ethyl acetate. The organic layer was dried over $Na_2SO_4$. Concentration and precipitation in diisopropyl ether gave the expected product (4.42 g, 50% as solid).

$^1$H-NMR (DMSO d6): 1.65 (s, 9H), 3.85 (s, 3H), 4.42 (s, 2H), 7.00 (d, 1H), 7.50 (d, 1H), 7.75 (d, 1H).

Preparation of (1H-indazole-3-yl)acetonitrile (20), (21) and (22)

Example 45

2-(Z/E)-2-(6-methoxy-1H-indazol-3-yl)-3-(4-methoxyphenyl) prop-2-ene nitrile

A solution of KOH at 40% in 3.5 ml of water and 7.1 ml ethanol was added dropwise to p-anisaldehyde (2.06 ml, 16.9 mmol) and {1-[(tert-butoxycarbonyl)oxy]-6-methoxy-1H-indazol-3-yl}acetonitrile in ethanol. When the reaction was complete, the mixture was filtered to obtain 3.53 g of the expected product (77% as solid).

$^1$H-NMR (DMSO d$_6$): 3.35 (s, 1H), 3.85 (s, 3H), 3.90 (s, 3H), 6.70-7.20 (m, 4H), 7.85-8.15 (m, 4H).

Using the same procedure but replacing p-anisaldehyde by cyclohexane carboxaldehyde, the following compound was obtained:

Example 46

2-(Z/E)-3-cyclohexyl-2-(6-methoxy-1H-indazol-3-yl) prop-2-enenitrile (55.4%).

$^1$H-NMR (DMSO d$_6$): 1.20-1.80 (m, 10H), 2.60-2.75 (m, 1H), 3.80 (s, 3H), 6.85 (dd, 1H), 6.95 (d, 1H), 7.15 (d, 1H), 7.85 (d, 1H), 13.20 (s, 1H).

Example 47

2-(6-methoxy-1H-indazol-3-yl)-3-(4-methoxyphenyl) propanenitrile

To 2-(6-methoxy-1H-indazol-3-yl)-3-(4-methoxyphenyl) prop-2-enenitrile (3.53 g, 11.56 mmol) dissolved in ethanol was added portionwise NaBH$_4$ (0.66 g, 17 mmol). The mixture was stirred at 70° C. overnight, then poured into water, acidified with concentrated HCl, extracted with ethyl acetate. The organic layer was dried over Na$_2$SO$_4$, filtered and concentrated. The oil was precipitated in ethanol and diisopropyl ether to give the expected product (3.18 g, as a white powder 85.3%).

$^1$H-NMR (DMSO d$_6$): 3.56 (s, 3H), 3.60-3.80 (m, 2H), 3.85 (s, 3H), 4.26 (t, 1H), 6.90-7.30 (m, 6H), 7.97 (d, 1H), 11.13 (s, 1H).

Using the same procedure but replacing 2-(Z/E)-2-(6-methoxy-1H-indazol-3-yl)-3-(4-methoxyphenyl)prop-2-enenitrile by 2-(Z/E)-3-cyclohexyl-2-(6-methoxy-1H-indazol-3-yl)prop-2-ene nitrile, the following compound was obtained:

Example 48

3-cyclohexyl-2-(6-methoxy-1H-indazol-3-yl) propanenitrile (97.5%).

$^1$H-NMR (DMSO d$_6$): 0.85-2.45 (m, 13H), 3.80 (s, 3H), 4.65 (t, 1H), 6.75 (dd, 1H), 6.90 (d, 1H), 7.65 (d, 1H), 12.85 (s, 1H).

Example 49

3-cyclohexyl-2-(6-hydroxy-1H-indazol-3-yl) propanenitrile 3-cyclohexyl-2-(6-methoxy-1H-indazol-3-yl) propanenitrile (1.61 g, 5.68 mmol) was dissolved in CH$_2$Cl$_2$ and cooled with an ice bath. BBr$_3$/CH$_2$Cl$_2$ 1M (8.6 ml, 8.52 mmol) was added to this mixture, which was stirred at 50° C., then poured onto saturated NaHCO$_3$ solution, extracted with ethylacetate, dried over Na$_2$SO$_4$, filtered, concentrated under vacuum and purified by flash chromatography (CH$_2$Cl$_2$/MeOH 98/2). Crystallisation from EtOH gave 780 mg of white crystals (51%). mp 175° C.

$^1$H-NMR (DMSO d$_6$): 0.80-2.05 (m, 13H), 4.65 (t, 1H), 6.70 (dd, 1H), 6.78 (d, 1H), 7.60 (d, 1H), 9.70 (s, 1H), 12.60 (s, 1H).

Preparation of Propanamides (23)

Using the same procedure as in Example 27 but replacing 3-(1-adamantyl)-6-methoxy-1H-indazole by:
2-(6-methoxy-1H-indazol-3-yl)-3-(4-methoxyphenyl) propanenitrile 3-cyclohexyl-2-(6-methoxy-1H-indazol-3-yl) propanenitrile the following compounds were respectively obtained:

Example 50

2-(1-acetyl-6-hydroxy-1H-indazol-3-yl)-3-(4-methoxyphenyl) propanamide (7.7%). mp=152° C.

$^1$H-NMR (DMSO d$_6$): 2.22 (s, 3H), 3.15 (q, 2H), 3.80 (s, 3H), 4.15 (m, 1H), 6.68 (dd, 1H), 6.80 (d, 1H), 6.85-7.05 (m, 3H), 7.20 (d, 2H), 7.52 (s, 1H), 7.80 (d, 1H), 12.53 (s, 1H).

Example 51

3-cyclohexyl-2-(6-hydroxy-1H-indazol-3-yl) propanamide (34%). mp=199° C.

$^1$H-NMR (DMSO d$_6$): 0.70-2.10 (m, 13H), 3.90 (t, 1H), 6.55 (d, 1H), 6.75 (s, 1H), 6.83 (s, 1H), 7.45 (s, 1H), 7.65 (d, 1H), 9.50 (s, 1H), 12.20 (s, 1H).

Preparation of the 1H-pyrano[4,3,2-cd]indazoles (25), (26) and (27)

Example 52

7-methoxy-3-(4-methoxyphenyl)-1H-pyrano[4,3,2-cd]indazole

Using the same procedure as in Example 12 but replacing cyclopentyl (4-benzyloxy-2-fluorophenyl)methanone by 5-chloro-7-methoxy-3-(4-methoxyphenyl)-4H-chromen-4-one (prepared following Kitagawa Chem Pharm Bull, 39, 1991, 2681), the expected product was obtained (as a solid, 84%).

$^1$H-NMR (DMSO, d$_6$): 3.60 (s, 3H), 3.80 (s, 3H), 6.60 (d, 2H), 6.80 (d, 2H), 7.10 (d, 1H), 7.30 (d, 1H), 7.80 (s, 1H).

Using the same procedure as in Example 49 but replacing 3-cyclohexyl-2-(6-methoxy-1H-indazol-3-yl) propanenitrile by 7-methoxy-3-(4-methoxyphenyl)-1H-pyrano[4,3,2-cd]indazole, the following compounds were obtained:

Example 53

3-(4-methoxy-phenyl)-1H-pyrano[4,3,2-cd]indazol-7-ol, hydrochloride (26%). mp 255° C.

$^1$H-NMR (DMSO d$_6$): 3.55 (s, 3H), 6.63 (m, 4H), 7.05 (d, 2H), 8.05 (s, 1H), 10.00 (s, 1H).

Example 54

3-(4-hydroxy-phenyl)-1H-pyrano[4,3,2-cd]indazol-7-ol, hydrochloride (15%). mp 111° C.

$^1$H-NMR (DMSO d$_6$): 6.45 (s, 2H), 6.65 (d, 2H), 7.10 (d, 2H), 8.00 (s, 1H), 10.00 (s, 1H).

Preparation of Oximes (28) and (30)

Example 55

1-adamantyl(2-chloro-4,6-dihydroxyphenyl)methanone

Boron tribromide 1M in $CH_2Cl_2$ was added to a solution of 1-adamantyl-(2-chloro-4,6-dimethoxyphenyl)methanone (7 g, 21.0 mmoles) and $CH_2Cl_2$ (30 ml). The mixture was warmed overnight and then poured into water, extracted with ethyl acetate, dried over $Na_2SO_4$ and concentrated under vacuum to give the expected product (1.9 g, 30%).
$^1$H-NMR (DMSO $d_6$): 1.00-1.90 (m, 15H), 6.25 (s, 1H), 6.30 (s, 1H), 10.00 (s, 2H).

Example 56

1-adamantyl(2-chloro-4,6-dihydroxyphenyl)methanone oxime 1-adamantyl-(2-chloro-4,6-dihydroxyphenyl)methanone (1.9 g, 6.2 mmoles), hydroxylamine hydrochloride (100 g) and pyridine (50 ml) were refluxed for 4 h. The mixture was concentrated under vacuum, poured into water, extracted with ethyl acetate, washed with HCl 1N, dried over $Na_2SO_4$ and concentrated under vacuum to give the crude product. Flash chromatography (AcOEt/toluene 3/7) gave the pure oxime (1 g as a solid, 50%).
$^1$H-NMR (DMSO $d_6$): 1.50-2.00 (m, 15H), 6.24 (s, 1H), 6.28 (s, 1H).

Using the same procedure but replacing 1-adamantyl-(2-chloro-4,6-dihydroxyphenyl)methanone by:
1-adamantyl-(4-benzyloxy-2-fluorophenyl)methanone
cycloheptyl (4-benzyloxy-2-fluorophenyl)methanone
the following compounds were respectively obtained:

Example 57

1-adamantyl-(4-benzyloxy-2-fluorophenyl)methanone oxime (32%).
$^1$H-NMR (DMSO $d_6$): 1.20-2.20 (m, 15H), 5.10 (s, 2H), 6.80 (dt, 1H), 6.90-7.17 (m, 2H), 7.20-7.60 (m, 5H), 10.55 (s, 1H).

Example 58 cycloheptyl (4-benzyloxy-2-fluorophenyl)methanone oxime (60%).
$^1$H-NMR (DMSO $d_6$): 1.10-2.00 (m, 12H), 2.10-2.20 (m, 1H), 5.10 (s, 2H), 6.67-6.85 (m, 1H), 6.90-7.15 (m, 2H), 7.25-7.50 (m, 5H), 10.47 (s, 1H).

Preparation of Benzisoxazoles (31), (32) and (34)

Example 59

6-benzyloxy-3-cyclohexyl-1,2-benzisoxazole

A solution of hydroxylamine hydrochloride (11.7 g) in warm water (100 ml) was poured into a mixture of cyclohexyl (4-benzyloxy-2-fluorophenyl)methanone (20.22 g, 64.7 mmol) and EtOH (54 ml). A solution of sodium hydroxide (11.13 g, 0.278 mol) in water (54 ml) was then added as rapidly as the reflux permitted. The reaction mixture was heated for 12 h and then most of the EtOH was removed by distillation. To the residue was added a solution of potassium hydroxide (8.7 g, 0.155 mol) in water (54 ml). The mixture was refluxed for 2 days, then cooled to about 6° C. and stirred vigorously. A white solid was obtained, which was thoroughly washed with water and triturated with diisopropyl ether. The benzisoxazole was obtained as a white powder (12.26 g, 62%) after filtration. mp 110° C.
$^1$H-NMR (DMSO $d_6$): 1.00-2.10 (m, 10H), 3.05 (m, 1H), 5.20 (s, 2H), 7.00 (dd, 1H), 7.25-7.55 (m, 6H), 7.75 (d, 1H).

Using the same procedure but replacing cyclohexyl (4-benzyloxy-2-fluorophenyl)methanone by cyclohexyl-(2-fluoro-4-hydroxy-5-methoxyphenyl)methanone, the following compound was obtained:

Example 60

3-cyclohexyl-6-hydroxy-5-methoxybenzisoxazole (50.5%).
$^1$H-NMR (DMSO $d_6$): 1.20-2.10 (m, 10H), 3.05 (m, 1H), 3.85 (s, 3H), 6.95 (s, 1H), 7.23 (s, 1H), 9.94 (s, 1H).

Example 61

3-(1-adamantyl)-4-chloro-1,2-benzisoxazol-6-ol

Diethylazodicarboxylate (0.92 g, 1.7 eq) in THF (20 ml) was added to a mixture of 1-adamantyl (2-chloro-4,6-dihydroxyphenyl)methanone oxime (1 g, 3.1 mmoles), triphenyl phosphine (1.4 g, 1.7 eq) in THF (20 ml) at 0° C. The mixture was stirred 2 h at 0° C., poured into water, extracted with ethylacetate, dried over $Na_2SO_4$ and concentrated under vacuum to give the crude product. Flash chromatography (AcOEt/toluene 1/9) and crystallisation from EtOH yielded the expected product (230 mg, 23%). mp 215° C.
$^1$H-NMR (CDCl$_3$): 1.50-2.10 (m, 15H), 6.23 (d, 1H), 6.32 (d, 1H).

Example 62

3-(1-adamantyl)-6-benzyloxy-1,2-benzisoxazole 1-adamantyl-(4-benzyloxy-2-fluorophenyl)methanone oxime (2.3 mg, 6 mM) in DMF (30 ml) was added at 0° C. dropwise under $N_2$, to a stirred suspension of NaH (0.61 g, 18 mM, 60% oil dispersion) in DMF (10 ml). After the complete addition, the reaction mixture was allowed to warm to room temperature and poured into $H_2O$. The precipitate was collected by filtration to give the expected product (2.06 g, 95%). mp 132° C.
$^1$H-NMR (DMSO $d_6$): 1.20-2.45 (m, 15H), 5.22 (s, 2H), 7.00 (d, 1H), 7.30-7.60 (m, 6H), 7.72 (d, 1H).

Using the same procedure but replacing 1-adamantyl-(4-benzyloxy-2-fluorophenyl)methanone oxime by cycloheptyl (4-benzyloxy-2-fluorophenyl)methanone oxime, the following compound was obtained Example 63

6-benzyloxy-3-cycloheptyl-1,2-benzisoxazole (90%). mp 80° C.
$^1$H-NMR (DMSO $d_6$): 1.30-2.20 (m, 12H), 3.25 (m, 1H), 5.21 (s, 2H), 7.00 (dd, 1H), 7.25-7.60 (m, 6H), 7.75 (d, 1H).

Using the same procedure as in Example 23 but replacing 6-benzyloxy-3-cyclopentyl-1H-indazole by:
3-(1-adamantyl)-6-benzyloxy-1,2-benzisoxazole
6-benzyloxy-3-cycloheptyl-1,2-benzisoxazole
6-benzyloxy-3-cyclohexyl-1,2-benzisoxazole
the following compounds were respectively obtained:

Example 64

3-(1-adamantyl)-1,2-benzisoxazol-6-ol (47.5%). mp 215° C.
$^1$H-NMR (DMSO $d_6$): 1.40-2.20 (m, 13H), 2.35 (s, 2H), 6.80 (dd, 1H), 6.92 (d, 1H), 7.58 (d, 1H), 10.28 (s, 1H).

Example 65

3-cycloheptyl-1,2-benzisoxazol-6-ol (48%). mp 156° C.
$^1$H-NMR (DMSO $d_6$): 1.20-2.20 (m, 12H), 3.18 (m, 1H), 6.80 (d, 1H), 6.90 (s, 1H), 7.65 (d, 1H), 10.25 (s, 1H).

Example 66

3-cyclohexyl-1,2-benzisoxazol-6-ol (37%). mp 181° C.
$^1$H-NMR (DMSO $d_6$): 1.10-2.10 (m, 10H), 3.02 (dt, 1H), 6.80 (dd, 1H), 6.90 (s, 1H), 7.68 (d, 1H), 10.25 (s, 1H).

Example 67

3-cyclohexyl-1,2-benzisoxazol-5,6-diol

Using the same procedure as in Example 49 but replacing 3-cyclohexyl-2-(6-methoxy-1H-indazol-3-yl) propanenitrile by 3-cyclohexyl-6-hydroxy-5-methoxybenzisoxazole, the expected product was obtained (48.4%). mp 177° C.
$^1$H-NMR (DMSO $d_6$): 1.20-2.05 (m, 10H), 3.05 (dt, 1H), 6.92 (s, 1H), 7.05 (s, 1H), 9.55 (br s, 2H).

Example 68

3-cyclohexyl-6-(2-piperidin-1-yl-ethoxy)-1,2-benzisoxazole

A mixture of 3-cyclohexyl-1,2-benzisoxazol-6-ol (2.69 g, 12 mmol), 1-(2-chloroethyl)-piperidine hydrochloride (2.39 g, 13 mmol) and $K_2CO_3$ (3.59 g, 26 mmol) in $CH_3CN$ (30 ml) was heated at reflux for 3 h and stirred at room temperature overnight. The reaction mixture was poured into $H_2O$ and extracted with EtOAc. The organic extract was washed with brine, dried ($Na_2SO_4$) and concentrated to give a residue (3.78 g). This residue was purified by flash chromatography (toluene/1,4-dioxane 8/2). Crystallisation from EtOH gave white crystals (0.53 g, 13.4%). mp 69° C.
$^1$H-NMR (DMSO $d_6$): 1.20-2.10 (m, 16H), 2.30-2.50 (m, 4H), 2.70 (t, 2H), 2.95-3.05 (dt, 1H), 4.15 (t, 2H), 6.95 (dd, 1H), 7.25 (d, 1H), 7.75 (d, 1H).

Example 69

Trihydroxybenzoin

Resorcinol (100 g, 0.91 mol) and 4-hydroxyphenylacetic acid (138.4 g, 0.91 mol) were dissolved into $BF_3Et_2O$ (346 ml, 2.73 mol) under $N_2$. The mixture was stirred and heated at 50-60° C. After complete reaction, the mixture was cooled to room temperature and poured into a large volume of iced water. The crude product was filtered off and dried to yield trihydroxybenzoin (70%). mp 211° C.
$^1$H-NMR (Acetone $d_6$): 4.12 (s, 2H), 6.78 (d, 2H), 6.91 (d, 1H), 7.13 (d, 2H), 7.54-7.6 (m, 2H), 8.21 (s, 1H), 8.35 (s, 1H), 8.70 (s, 1H).

Example 70

1-[2-hydroxy-4-(tetrahydro-2H-pyran-2-yloxy)phenyl]-2-[4-(tetrahydro-2H-pyran-2-yloxy)phenyl]ethanone To a cooled (0-5° C.) suspension of trihydroxybenzoin (100 g, 0.41 mol) and, as a catalyst, TsOH (0.062 g) in toluene (350 ml), a solution of dihydropyran (DHP) (150 ml, 1.64 mol) was slowly added. The reaction mixture became homogenous and was stirred at room temperature for 1 h. Triethylamine was added and the solvent was evaporated under reduced pressure. The brown oil crystallized upon trituration with hot isopropanol (1.2 l) and a white solid was collected (182 g, 90%).
$^1$H-NMR ($CDCl_3$): 1.40-2.05 (m, 12H), 3.40-3.60 (m, 2H), 3.65-3.90 (m, 2H), 4.05 (s, 2H), 5.30 (t, 1H), 5.40 (t, 1H), 6.46 (dd, 1H), 6.54 (d, 1H), 6.94 (d, 2H), 7.10 (d, 2H), 7.68 (d, 1H), 12.52 (s, 1H).

Example 71

1-[2-hydroxy-4-tetrahydro-2H-pyran-2-yloxy)phenyl]-2-[4-(tetrahydro-2H-pyran-2-yloxy)phenyl]ethanone oxime A mixture of 1-[2-hydroxy-4-(tetrahydro-2H-pyran-2-yloxy)]-2-[4-(tetrahydro-2H-pyran-2-yloxy)phenyl]ethanone (5 g, 12 mmol) and $H_2NOH$, HCl (8.59 g, 12.3 mmol) was stirred for 24 h in pyridine (65 ml) at room temperature. The reaction mixture was poured into a large volume of 99/1 $H_2O$/triethylamine and was then extracted with EtOAc. The organic solution was washed with brine. After drying over $Na_2SO_4$, EtOAc was evaporated. The residue was purified by flash column chromatography (toluene/1,4-dioxane 90/1+TEA 1%) to provide a colorless oil (5.05 g, 97%).
$^1$H-NMR (DMSO $d_6$): 1.30-2.00 (m, 12H), 3.40-3.60 (m, 2H), 3.60-3.80 (m, 2H), 4.12 (s, 2H), 5.38 (t, 1H), 5.45 (t, 1H), 6.48 (d, 1H), 6.50 (s, 1H), 6.93 (d, 2H), 7.05-7.30 (m, 3H), 7.40 (d, 1H), 11.63 (s, 1H), 11.85 (s, 1H).

Example 72

6-(tetrahydro-2H-pyran-2-yloxy)-3-[4-(tetrahydro-2H-pyran-2-yloxy)benzyl]-1,2-benzisoxazole Using the same procedure as in Example 61 but replacing 1-adamantyl-(2-chloro-4,6-dihydroxyphenyl)methanone oxime by 1-[2-hydroxy-4-(tetrahydro-2H-pyran-2-yloxy)phenyl]-2-[4-(tetrahydro-2H-pyran-2-yloxy)phenyl]ethanone oxime, the expected product was obtained (25%).
$^1$H-NMR (DMSO $d_6$): 1.40-2.10 (m, 12H), 3.40-3.85 (m, 4H), 4.25 (s, 2H), 5.39 (s, 1H), 5.61 (s, 1H), 6.90-7.10 (m, 3H), 7.20-7.35 (m, 3H), 7.55 (d, 1H)

Example 73

3-(4-hydroxybenzyl)-1,2-benzisoxazol-6-ol 6-(tetrahydro-2H-pyran-2-yloxy)-3-[4-(tetrahydro-2H-pyran-2-yloxy)benzyl]-1,2-benzisoxazole (3.85 mmol) and paratoluenesulfonic acid (APTS, catalytic amount) were dissolved in methanol (20 ml). After reaction at 60-70° C. for 3 h, the reaction mixture was cooled to room temperature and poured into saturated NaHCO$_3$ and extracted with EtOAc. After washing (H$_2$O) and drying (MgSO$_4$), the extract was concentrated. The crude product was purified by flash chromatography (toluene/1,4-dioxane 8/2) and crystallised to give an off-white crystal (0.58 g, 31%). mp 178° C.

$^1$H-NMR (DMSO d$_6$): 4.11 (s, 2H), 6.69 (d, 2H), 6.75 (dd, 1H), 6.90 (d, 1H), 7.13 (d, 2H), 7.48 (d, 1H), 9.80 (s, 2H).

Preparation of Benzisoxazole Sulfamate (33)

Using the same procedure as in Example 33 but replacing 6-benzyloxy-3-cycloheptyl-1H-indazole by:
3-(1-adamantyl)-1,2-benzisoxazol-6-ol
3-cycloheptyl-1,2-benzisoxazol-6-ol
3-cyclohexyl-1,2-benzisoxazol-6-ol
the following compounds were respectively obtained:

Example 74

3-(1-adamantyl)-1,2-benzisoxazol-6-yl sulfamate (82%). mp 87° C.
$^1$H-NMR (DMSO d$_6$): 1.50-2.45 (m, 15H), 7.28 (dd, 1H), 7.63 (d, 1H), 7.96 (d, 1H), 8.15 (s, 2H).

Example 75

3-cycloheptyl-1,2-benzisoxazol-6-yl sulfamate (54%). mp 82° C.
$^1$H-NMR (DMSO d$_6$): 1.40-2.10 (m, 12H), 3.32 (m, 1H), 7.30 (d, 1H), 7.60 (d, 1H), 8.05 (d, 1H), 8.15 (s, 2H).

Example 76

3-cyclohexyl-1,2-benzisoxazol-6-yl sulfamate (46%). mp 145° C.
$^1$H-NMR (DMSO d$_6$): 1.20-2.20 (m, 10H), 3.15 (dt, 1H), 7.25 (dd, 1H), 7.62 (d, 1H), 8.05 (d, 1H), 8.15 (s, 2H).

Preparation of Benzisoxazoles (36) (37) and (38)

Example 77

2-(Z/E)-(6-methoxy-1,2-benzisoxazol-3-yl)-3-(4-methoxyphenyl)prop-2-enenitrile

A solution of 40% KOH/H$_2$O (3 ml) and EtOH (4.8 ml) was added slowly to a heterogenous mixture of (6-methoxy-1,2-benzisoxazol-3-yl)acetonitrile (2.4 g, 12.7 mmoles), prepared following H. Uno (Chem. Pharm. Bull., 24 (4), 632-643, 1976), 4-methoxybenzaldehyde (1.1 eq, 14 mmoles, 1.8 g) and EtOH (24 ml) at room temperature. The mixture was stirred at room temperature for 1 h and the precipitate was filtered under vacuum, washed with water and EtOH, to give pure 2-(Z/E)-(6-methoxy-1,2-benzisoxazol-2-yl)-3-(4-methoxy-phenyl)-prop-2-enenitrile (3.15 g, 81%).

$^1$H-NMR (acetone d$_6$)=3.94 (s, 3H), 3.97 (s, 3H), 7.08 (dd, 1H), 7.15 (d, 2H), 8.05-8.30 (m, 4H).

Using the same procedure but replacing 4-methoxybenzaldehyde by 4-hydroxybenzaldehyde the following compound was obtained:

Example 78

2-(Z/E)-3-(4-hydroxyphenyl)-2-(6-methoxy-1,2-benzisoxazol-3-yl)prop-2-enenitrile (86%). mp>380° C.
$^1$H-NMR (DMSO d$_6$): 3.85 (s, 3H), 6.15 (d, 2H), 7.00 (d, 1H), 7.25 (s, 1H), 7.70 (s, 3H), 8.00 (d, 1H).

Example 79

2-(6-methoxy-1,2-benzisoxazol-3-yl)-3-(4-methoxyphenyl) propanenitrile

NaBH$_4$ (1.05 eq, 0.2 g, 5.15 mmoles) was added to an heterogenous solution of 2-(Z/E)-(6-methoxy-1,2-benzisoxazol-3-yl)-3-(4-methoxy-phenyl)prop-2-enenitrile (1.5 g, 4.9 mmoles) and EtOH (20 ml). The mixture was heated at 50° C. for 1 h, and acidified at pH 1 with HCl 1N, extracted with AcOEt, dried over Na$_2$SO$_4$ and concentrated under vacuum to give pure 2-(6-methoxy-1,2-benzisoxazol-3-yl)-3-(4-methoxyphenyl) propanenitrile (1.5 g, 100%).

$^1$H-NMR (CDCl$_3$)=3.35 (d, 2H), 3.80 (s, 3H), 3.90 (s, 3H), 4.45 (t, 1H), 6.84 (d, 2H), 6.93 (dd, 1H), 7.02 (d, 1H), 7.04 (d, 2H), 7.50 (d, 1H).

Example 80

2-(6-hydroxy-1,2-benzisoxazol-3-yl)-3-(4-hydroxyphenyl) propanenitrile

To a solution of 2-(6-methoxy-1,2-benzisoxazol-3-yl)-3-(4-methoxyphenyl)propanenitrile (1.5 g, 4.9 mmoles) in CH$_2$Cl$_2$ (100 ml) under N$_2$, was added BBr$_3$ 1M in CH$_2$Cl$_2$ (4 eq, 20 ml). The mixture was refluxed for 2 h, poured into water and extracted with EtOAc, dried over Na$_2$SO$_4$, filtered and concentrated under vacuum to give the crude product. Purification by flash chromatography (CH$_2$Cl$_2$/MeOH 98/2) and crystallisation from EtOH yielded the expected crystals (850 mg, 62%). mp 214° C.

$^1$H-NMR (DMSO d$_6$): 3.25 (m, 2H), 5.10 (t, 1H), 6.65 (d, 2H), 6.90 (d, 1H), 7.00 (d, 2H), 7.06 (s, 1H), 7.70 (d, 1H), 9.35 (s, 1H), 10.50 (s, 1H).

Using the same procedure as in Example 77 but replacing 4-methoxybenzaldehyde by:
3-fluoro-4-methoxybenzaldehyde
4-methoxy-2-methyl-benzaldehyde
3-methoxy-benzaldehyde
4-fluorobenzaldehyde
cyclohexanal
3,4-dimethoxybenzaldehyde
and then using the same procedures as described in Examples 79 and 80, the following compounds were respectively obtained:

Example 81

2-(6-hydroxy-1,2-benzisoxazol-3-yl)-3-(3-fluoro-4-hydroxyphenyl)-propanenitrile (56%). mp 201° C.
$^1$H-NMR (DMSO d$_6$): 3.25 (m, 2H), 5.15 (t, 1H), 6.70-7.20 (m, 5H), 7.72 (d, 1H), 9.82 (s, 1H), 10.55 (s, 1H).

Example 82

2-(6-methoxy-1,2-benzisoxazol-3-yl)-3-(4-hydroxy-2-methylphenyl)-propanenitrile (15%). mp 131° C.
$^1$H-NMR (acetone d$_6$): 2.11 (s, 3H), 3.28 (d, 2H), 3.80 (s, 3H), 4.72 (t, 1H), 6.40-6.60 (m, 2H), 6.85 (dd, 1H), 7.00 (d, 1H), 7.10 (d, 1H), 8.09 (s, 1H).

Example 83

2-(6-hydroxy-1,2-benzisoxazol-3-yl)-3-(3-hydroxyphenyl) propanenitrile (20%).
$^1$H-NMR (acetone d$_6$): 3.25-3.60 (m, 2H), 4.90 (t, 1H), 6.60-7.25 (m, 6H), 7.70 (d, 1H), 8.80 (br s, 1H).

Example 84

2-(6-hydroxy-1,2-benzisoxazol-3-yl)-3-(4-fluorophenyl) propanenitrile (35%). mp 152° C.
$^1$H-NMR (DMSO d$_6$): 2.40-2.70 (m, 2H), 3.95 (t, 1H), 4.25 (s, 1H), 5.90-6.50 (m, 6H), 6.70 (d, 1H).

Example 85

2-(6-hydroxy-2-benzisoxazol-3-yl)-3-cyclohexylpropanenitrile (63%). mp 111° C.
$^1$H-NMR (acetone d$_6$): 0.80-2.10 (m, 13H), 4.56 (dd, 1H), 6.90 (dd, 2H), 7.02 (d, 1H), 7.67 (d, 1H), 9.38 (s, 1H).

Example 86

2-(6-hydroxy-1,2-benzisoxazol-3-yl)-3-(3,4-dihydroxyphenyl) propanenitrile (56%). mp 154° C.
$^1$H-NMR (DMSO d$_6$): 3.00-3.35 (m, 2H), 5.06 (t, 1H), 6.50 (dd, 1H), 6.55-6.75 (m, 2H), 6.90 (dd, 1H), 7.00 (dd, 1H), 7.70 (d, 1H), 8.90 (br s, 1H).

Preparation of Benzisoxazoles (40) (41) (42) and (43)

Example 87

3-methyl-6-[(tert-butyl(dimethyl)silyl)oxy]-1,2-benzisoxazole 3-methyl-1,2-benzisoxazol-6-ol (10 g, 67 mmoles) (prepared following M. A. Elkasaby, *Indian J. Chem.*, 1987, 26, 620) and DMF (50 ml) were added to a mixture of tert-butyldimethylsilyl chloride (1.05 eq, 10.6 g), imidazole (2.5 eq, 11.4 g) and DMF (100 ml) under N$_2$. The mixture was then stirred at room temperature for 1 h, poured into water and extracted with ethyl acetate, dried over Na$_2$SO$_4$, filtered and concentrated under vacuum to give a crude product. Flash chromatography (AcOEt/Toluene 18/85 with 0.1% TEA) gave 6-[(tert-butyl(dimethyl)silyl) oxy]-3-methyl-1,2-benzisoxazole (17.1 g, 97%).
$^1$H-NMR (CDCl$_3$ d$_1$): 0.20 (s, 6H), 1.00 (s, 9H), 2.60 (s, 3H), 6.80 (dd, 1H), 6.95 (d, 1H), 7.45 (d, 1H).

Example 88

3-(bromomethyl)-6-[(tert-butyl(dimethyl)silyl)oxy]-1,2-benzisoxazole

NBS (12.7 g, 71.5 mmoles) and benzyl peroxide (1.6 g, 6.5 mmoles) were added to a mixture of 3-methyl-6-[(tert-butyl (dimethyl)silyl)oxy]-1,2-benzisoxazole (17.1 g, 65 mmoles) and CCl$_4$ (200 ml). The mixture was refluxed overnight and the precipitate was filtered, washed with CCl$_4$ and purified by flash chromatography (AcOEt/Toluene 1/9 with 0.1% TEA) to give 3-(bromomethyl)-6-[(tert-butyl(dimethyl)silyl)oxy]-1,2-benzisoxazole (15.1 g, 68%).
$^1$H-NMR (CDCl$_3$ d$_1$): 0.25 (s, 6H), 1.00 (s, 9H), 4.57 (s, 2H), 6.88 (dd, 1H), 7.02 (d, 1H), 7.55 (d, 1H).

Example 89

3-(6-[(tert-butyl)silyl)oxy]-1,2-benzisoxazol-3-yl)-2-(4-methoxyphenyl) propanenitrile A solution of n-BuLi 2.0M in THF (9.7 mmoles) was slowly added to a solution of diisopropylamine (1.3 ml, 1.05 eq) and dry THF (10 ml) at −20° C. under N$_2$. The mixture was stirred for 30 min at −20° C., then 4-methoxybenzonitrile (1.3 g, 8.8 mmoles) and dry THF (10 ml) were slowly added at −78° C. The mixture was stirred for 30 min at −78° C., then 3-(bromomethyl)-6-[(tert-butyl(dimethyl)silyl)oxy]-1,2-benzisoxazole (3 g, 8.8 mmoles) and dry THF (10 ml) were slowly added. The mixture was then stirred for 30 min at room temperature, poured into water, extracted with AcOEt, dried over Na$_2$SO$_4$, and purified by flash chromatography (AcOEt/Heptane 2/8 with 0.1% TEA) to give 3-(6-[(tert-butyl)dimethylsilyl)oxy]-1,2-benzisoxazol-3-yl)-2-(4-methoxyphenyl) propanenitrile (1 g, 28%).
$^1$H-NMR (CDCl$_3$ d$_1$): 0.20 (s, 6H), 1.00 (s, 9H), 3.25-3.65 (m, 2H), 3.70-4.48 (t, 1H), 6.80-7.60 (m, 7H).

Example 90

3-(6-hydroxy-1,2-benzisoxazol-3-yl)-2-(4-methoxyphenyl)propanenitrile

A solution of nBu$_4$F 1N in THF was added to a mixture of 3-(6-[(tert-butyl)silyl)oxy]-1,2-benzisoxazol-3-yl)-2-(4-methoxyphenyl)propanenitrile (1.0 g, 2.45 mmoles) in dry THF (20 ml) at room temperature. The mixture was then stirred at room temperature for 2 h and then poured into water and extracted with ethyl acetate, dried over Na$_2$SO$_4$, filtered, and concentrated under vacuum. The crude product was purified by flash chromatography (AcOEt/Toluene 2/8) and crystallisation from MeOH/cyclohexane yielded the expected product (210 mg, 30%).
$^1$H-NMR (DMSO d$_6$)=3.00-3.50 (m, 2H), 5.05 (t, 1H), 6.60 (d, 2H), 6.90 (dd, 1H), 7.00 (d, 2H), 7.05 (s, 1H), 7.70 (d, 1H), 9.40 (s, 1H), 10.50 (s, 1H).

Preparation of Benzisothiazoles (45) and (46)

Example 91 cyclohexyl (4-benzyloxy-2-benzylthiophenyl)methanone

A solution of phenylmethanethiol (2.35 ml, 20 mmoles) in THF (10 ml) was slowly added to a mixture of potassium tert-butoxide (2.24 g, 20 mmoles) in THF (80 ml) under N$_2$ at room temperature. The mixture was stirred for 15 min at room temperature and cyclohexyl (4-benzyloxy-2-fluorophenyl) methanone (6.5 g, 20 mmoles) in THF (10 ml) was slowly added. The mixture was heated for 2 h at 50° C. and poured into an aqueous solution of NH$_4$Cl, extracted with ethyl acetate, dried over Na$_2$SO$_4$ and concentrated under vacuum. The crude product was purified by flash chromatography (Heptane/AcOEt 90/10 with 0.1% TEA) to give cyclohexyl (4-benzyloxy-2-benzylthiophenyl)methanone (8.3 g, 100%).

$^1$H-RMN (DMSO d$_6$): 1.00-1.85 (m, 10H), 3.10-3.30 (m, 1H), 4.15 (s, 2H), 5.19 (s, 1H), 6.85 (dd, 1H), 7.05 (d, 1H), 7.15-7.60 (m, 10H), 7.90 (d, 1H).

Example 92

6-benzyloxy-3-cyclohexyl-1,2-benzisothiazole

Sulfuryl chloride (1.77 ml, 2.2 mmoles) was slowly added to a solution of cyclohexyl (4-benzyloxy-2-benzylthiophenyl)methanone (8.77 g, 21 mmoles) in CH$_2$Cl$_2$ (80 ml) at 0° C. The mixture was stirred for 2 h at room temperature and then concentrated under vacuum. THF (80 ml) was added to the mixture and then EtOH (80 ml) saturated with ammoniac was slowly added at 0° C. The mixture was stirred overnight at room temperature, poured into water, extracted with ethyl acetate, dried over Na$_2$SO$_4$, filtered and concentrated under vacuum to give a crude product. Flash chromatography (heptane/AcQEt 98/2) gave 6-benzyloxy-3-cyclohexyl-1,2-benzisothiazole (3.55 g, 52%).

$^1$H-NMR (DMSO d$_6$): 1.10 to 2.00 (m, 10H), 3.25 (dt, 1H), 5.20 (s, 2H), 7.12 (dd, 1H), 7.25 to 7.55 (m, 5H), 7.75 (d, 1H), 8.02 (d, 1H).

Example 93

3-cyclohexyl-1,2-benzisothiazol-6-ol

A solution of boron tribromide 1M in CH$_2$Cl$_2$ (11.9 ml, 11.9 mmoles) was slowly added to a solution of 6-benzyloxy-3-cyclohexyl-1,2-benzisothiazole (3.5 g, 10 mmoles) in CH$_2$Cl$_2$ (50 ml) at 0° C. The mixture was stirred at room temperature for 15 min and poured into water. The precipitate was filtered, dried and crystallised from EtOH to give pure 3-cyclohexyl-1,2-benzisothiazol-6-ol (940 mg, 40.3%). mp 190° C.

$^1$H-NMR (DMSO d$_6$): 1.10 to 2.10 (m, 10H), 3.20 (dt, 1H), 6.95 (dd, 1H), 7.40 (d, 1H), 7.93 (d, 1H), 10.18 (s, 1H).

Using the same procedures as in Examples 91 to 93 but replacing cyclohexyl (4-benzyloxy-2-fluorophenyl)methanone by cyclopentyl (4-benzyloxy-2-fluorophenyl)methanone, the following compound was obtained:

Example 94

3-cyclopentyl-1,2-benzisothiazol-6-ol mp 130° C.
$^1$H-NMR (DMSO d$_6$): 1.50 to 2.20 (m, 8H), 3.62 (m, 1H), 6.95 (dd, 1H), 7.35 (d, 1H), 7.92 (d, 1H), 10.18 (s, 1H).

Preparation of Benzisothiazole Sulfamates (47) and (48)

Example 95

3-cyclohexyl-1,2-benzisothiazol-6-yl sulfamate

Sulfamoyl chloride (780 mg, 6.76 mmol) was added by portions to a mixture of 3-cyclohexyl-1,2-benzisothiazol-6-ol (790 mg, 3.38 mmoles) and dimethylacetamide (15 ml) at 0° C. The mixture was stirred for 30 min at 0° C. and then at room temperature overnight, poured into water and extracted with ethyl acetate, dried over Na$_2$SO$_4$ and concentrated under vacuum.

The crude product was purified by flash chromatography (Toluene/1,4-dioxan 9/1) and crystallised from EtOH/pentane to give the expected product (620 mg, 59%). mp 150° C.

$^1$H-NMR (DMSO d$_6$): 1.20 to 2.05 (m, 10H), 3.30 (m, 1H), 7.40 (dd, 1H), 8.10 (d, 1H), 8.15 (s, 2H), 8.25 (d, 1H).

Using the same procedure but replacing 3-cyclohexyl-1,2-benzisothiazol-6-ol by 3-cyclopentyl-1,2-benzisothiazol-6-ol, the following compound was obtained:

Example 96

3-cyclopentyl-1,2-benzisothiazol-6-yl sulfamate mp 132° C.
$^1$H-NMR (DMSO d$_6$): 1.55 to 2.25 (m, 8H), 3.65-3.85 (m, 1H), 7.4 (dd, 1H), 8.10 (s, 1H), 8.15 (s, 2H), 8.23 (d, 1H).

Example 97

3-cyclohexyl-1,1-dioxido-1,2-benzisothiazol-6-yl sulfamate

Hydrogen peroxide (0.6 ml) was slowly added to a mixture of sulfamic acid, 3-cyclohexyl-1,2-benzisothiazol-6-yl-ester (1 g, 3.2 mmoles), trifluoroacetic acid (2 ml) and dichloromethane (20 ml) at room temperature. The mixture was then stirred for 2 h and then poured into water. The precipitate was filtered and purified by flash chromatography (Toluene/1,4-dioxan 85/15) to give after crystallisation a solid (70 mg, 6%). mp 170° C.

$^1$H-NMR (DMSO d$_6$): 1.10 to 2.20 (m, 10H), 7.25 (dd, 1H), 8.07 (d, 1H), 8.25 (s, 1H), 8.43 (s, 1H).

Pharmacological Test Results

Subtype Estrogen Receptor Binding In Vitro

The method was derived from those described for rat uterus (Botella J. et al, J Endocrinol Invest, 1990, 13: 905-910) and human Ishikawa cell (Botella J., J Steroid Biochem Molec Biol, 1995, 55: 77-84) estrogen receptors. Relative binding affinities (RBA) were determined by competitive radiometric binding assays, using purified full-length recombinant human ERα and ERβ (PanVera, Madison, Wis.). Receptors were incubated in Tris buffer (10 mM Tris, 2 mM DTT, 1 mg/BSA, 10% Glycerol, pH 7.5 with HCl) at 4° C. for 18-20 hours with 2 nM of [$^3$H]-E$_2$ with or without increasing concentrations of test compound from 1 nM to 10 µM. Non-specific binding was measured in the presence of a 500-fold excess of unlabeled E$_2$. Separation of bound and free $^3$H-E$_2$ fractions was achieved with dextran (0.25%) coated charcoal (2.5%) in Tris-EDTA buffer. After shaking for a few seconds and centrifugation at 1500 g and 4° C. for 10 minutes, 150 µl/well of Optiphase 'Super Mix' scintillation liquid was mixed with 50 µl of supernatant of each sample and the radioactivity was measured in a MicroBeta counter (Wallac, Turku, Finland). Data were evaluated by a sigmoidal dose-response curve (Prism, GraphPad Software Inc.) to estimate the concentration of competitor at half-maximal specific binding (IC$_{50}$). RBA of each competitor was calculated as the ratio of IC$_{50}$s of E$_2$ and competitor, and the RBA value for E$_2$ was arbitrarily set at 100%. The selectivity for ERα and ERβ was obtained from the ratio R of the IC$_{50}$ for ERα to the IC$_{50}$ for ERβ for each test compound.

TABLE 1

Estrogen Receptor α and β binding assays

| Compound | ER | $IC_{50}$ (nM) Mean ± S.E.M | RBA (%) Mean ± S.E.M | n | R ($IC_{50}$s) αβ |
|---|---|---|---|---|---|
| $E_2$ | α | 1.6 ± 0.1 | 100.0 ± | 59 | 0.8 |
|  | β | 2.1 ± 0.1 | 100.0 ± | 59 |  |
| Ex 23 | α | 1332.0 ± 267.8 | 0.2 ± 0.05 | 4 | 31.9 |
|  | β | 41.8 ± 7.1 | 10.4 ± 4.0 | 4 |  |
| Ex 24 | α | 159.1 ± 23.7 | 1.2 ± 0.2 | 9 | 15.6 |
|  | β | 10.2 ± 0.9 | 24.6 ± 4.3 | 9 |  |
| Ex 31 | α | 119.0 ± 45.2 | 3.1 ± 0.8 | 4 | 3.3 |
|  | β | 36.2 ± 18.7 | 17.7 ± 5.1 | 4 |  |
| Ex 35 | α | 2686.0 ± 593.0 | 0.1 ± 0.02 | 4 | 10.8 |
|  | β | 248.0 ± 48.7 | 0.9 ± 0.1 | 4 |  |
| Ex 40 | α | 1483.0 ± 1177.6 | 0.1 ± 0.02 | 5 | 7.9 |
|  | β | 187.6 ± 34.0 | 1.0 ± 0.2 | 5 |  |
| Ex 65 | α | 75.3 ± 5.4 | 2.5 ± 0.6 | 4 | 3.7 |
|  | β | 20.2 ± 4.2 | 13.2 ± 3.1 | 4 |  |
| Ex 66 | α | 260.0 ± 40.1 | 1.1 ± 0.2 | 4 | 5.8 |
|  | β | 44.6 ± 7.7 | 9.4 ± 3.1 | 4 |  |
| Ex 73 | α | 2912.3 ± 317.8 | 0.1 ± 0.0 | 3 | 6.0 |
|  | β | 484.8 ± 157.7 | 1.0 ± 0.3 | 4 |  |
| Ex 80 | α | 67.5 ± 5.0 | 3.4 ± 0.4 | 8 | 9.0 |
|  | β | 7.5 ± 0.7 | 43.0 ± 7.8 | 8 |  |
| Ex 81 | α | 139.3 ± 33.9 | 2.4 ± 0.7 | 4 | 9.7 |
|  | β | 14.4 ± 5.3 | 35.9 ± 14.0 | 4 |  |
| Ex 84 | α | 2300.8 ± 445.6 | 0.1 ± 0.03 | 4 | 18.7 |
|  | β | 122.9 ± 25.9 | 2.5 ± 0.4 | 4 |  |
| Ex 86 | α | 1894.0 ± 364.8 | 0.2 ± 0.03 | 4 | 14.1 |
|  | β | 134.8 ± 31.0 | 2.4 ± 0.4 | 4 |  |
| Ex 93 | α | 88.6 ± 11.7 | 1.3 ± 0.2 | 4 | 2.3 |
|  | β | 37.8 ± 5.4 | 5.1 ± 0.8 | 4 |  | n = number of assays

Estrogenic and Anti-Estrogenic Activities In Vitro

The estrogenic and anti-estrogenic potentials of new compounds were evaluated using the induction of alkaline phosphatase (APase) activity, an estrogen specific response in human endometrial adenocarcinoma Ishikawa cells (Botella J., J Steroid Biochem Molec Biol, 1995, 55: 77-84; Littlefield et al., Endocrinology, 1990, 127: 2757-2762).

Ishikawa cells were routinely grown as monolayers in Dulbecco's Modified Eagle's medium (DMEM) containing 4 mM Glutamax I and supplemented with 10% of decomplemented fetal calf serum (dFCS) and antibiotics. They were maintained in a humidified atmosphere of 5% $CO_2$ and 95% air, at 37±0.1° C. Stocks were performed once a week to maintain continuous exponential growth.

For studies, Ishikawa cells were plated into 96-well microplates. The next day, the medium was changed to a phenol red-free DMEM containing 5% dFCS stripped of endogenous estrogens by dextran coated charcoal treatment. Twenty-four hours later, the medium was renewed and the relevant controls and test compounds, diluted appropriately in estrogen-free DMEM, were added either alone (estrogenic effect) or with $10^{-8}$ M $E_2$ (anti-estrogenic effect) to the plated cells and incubated for four days. For each compound, the tested concentrations ranged from $10^{-12}$ M to $10^{-5}$ M, and the final vehicle concentration did not exceed 0.1%.

At the end of the incubation period, APase activity was assayed by a method involving the hydrolysis of p-nitrophenyl phosphate to p-nitrophenol at pH 9.8 and spectrophotometric determination of the product at 405 nm.

In brief, the microplates were first rinsed twice with cold phosphate buffered solution and then placed at −80° C. for at least 15 minutes. After thawing at room temperature for 5-10 minutes, the plates were put on ice and 50 µl ice-cold solution containing 5 mM p-nitrophenyl phosphate was added to each well. The plates were warmed to room temperature to allow for the development of the enzymatic reaction ($t_0$). After a 15 to 60 minute incubation period, the intensity of the yellow color generated by the production of p-nitrophenol was measured into each well at 405 nm using a microplate reader (Wallac, model 1420 Victor²). For each tested concentration, APase activity, reflected by absorbance, was first expressed as fold increase over control (FI) and then as percentage of $E_2$ activity ($10^{-8}$ M) chosen equal to 100%. Sigmoidal dose-response curves were plotted and $EC_{50}$ (estrogenic effect) and $IC_{50}$ (anti-estrogenic effect) values were calculated for each compound.

TABLE 2

Estrogenic and anti-estrogenic activities In vitro

| | Estrogenic activity | | Anti-estrogenic activity | |
|---|---|---|---|---|
| Compound | $EC_{50}$ (nM) ± S.E.M | n | $IC_{50}$ (nM) ± S.E.M | n |
| $E_2$ | 0.1 ± 0.05 | 3 | ± | 1 |
| Ex 23 | 1695 ± 168 | 4 | ND ± | 1 |
| Ex 24 | 136.3 ± 1.2 | 4 | ND ± | 1 |
| Ex 31 | 30.8 ± 0.5 | 4 | ND ± | 1 |
| Ex 35 | 373.8 ± 43.0 | 3 | ND ± | 1 |
| Ex 40 | 131.9 ± 4.7 | 4 | ND ± | 1 |
| Ex 65 | 51.7 ± 6.2 | 4 | ND ± | 1 |
| Ex 66 | 220.6 ± 14.0 | 4 | ND ± | 1 |
| Ex 73 | ND ± | 4 | ND ± | 1 |
| Ex 80 | 147.3 ± 39.9 | 4 | ND ± | 4 |
| Ex 81 | ND ± | 4 | ND ± | 1 |
| Ex 84 | 322.5 ± 20 | 4 | ND ± | 2 |
| Ex 86 | ND ± | 4 | ND ± | 1 |
| Ex 93 | 123.8 ± 8.9 | 4 | — ± | 1 | n = number of assays; ND = not detected; — not determined

Proliferative Activity In Vitro

The proliferative effect of the compounds of the invention was evaluated on human breast cancer cell line MCF-7 by measuring the number of viable cells after 6 days of treatment.

MCF-7 cells were routinely cultured as monolayers in Dulbecco's modified Eagle's medium (DMEM) containing 4 mM Glutamax and 4.5 g/l glucose and supplemented with 5% (v/v) decomplemented fetal calf serum (dFCS) and antibiotics.

Cells were plated at $2.10^6$ cells/75 cm² flasks and incubated at 37° C. in a humidified atmosphere containing 5% $CO_2$. They were passaged once weekly to maintain continuous exponential growth. Forty eight hours before the start of an experiment, near-confluent cells were changed to a phenol red free DMEM containing 5% steroid-stripped dFCS by dextran coated charcoal treatment (DCC-DMEM). On the day of the experiment, cells were harvested by brief exposure to trypsin and plated in DCC-DMEM in 96-well microplates at a density of $4.10^3$ cells/well. The next day, the medium was renewed and test compounds, diluted appropriately in estrogen-free DMEM, were added and incubated for six days. For each compound, the tested concentrations ranged from $10^{-12}$ M to $10^{-5}$ M and the final vehicle concentration did not exceed 0.1% (v/v). At the end of the incubation period, cell proliferation was evaluated by quantitation of the cellular ATP content which signals the presence of metabolically active cells.

ATP Assay

The assay, based on the ATP-dependent luciferase reaction, enables generation of a luminescent signal proportional to the amount of ATP present. As there is a linear relationship between the amount of ATP and the number of viable cells present in culture, the luminescent signal allowed to precisely evaluate cell proliferation (Crouch, S. P. M. et al. J. Immunol. Meth., 1993, 160, 81; Kangas, L. et al. Med. Biol. 1984, 62, 338; Petty, R. D. et al. J. Biolum. Chemilum. 1995, 10, 29).

In brief, the microplates were inverted to discard the culture medium and 100 µl of fresh medium was added into each well. The microplates were equilibrated at room temperature for approximately 30 minutes. 100 µl of luciferase reagent was added into each well and contents were mixed for 2 minutes to induce cell lysis. The plates were incubated at room temperature for 10 minutes to stabilize luminescence signal.

Luminescence was recorded using a microplate reader (Wallac, model 1420 Victor$^2$) and results were expressed as percentage of the control luminescence. Sigmoidal dose-response curves were plotted and $EC_{50}$ values were calculated for each compound in order to evaluate their proliferative potency.

TABLE 3

Proliferative activities in MCF-7 cells

| | Cell proliferation | | | |
|---|---|---|---|---|
| Compound | $EC_{50}$ (nM) ± S.E.M | n | Effect at $10^{-8}$ M (% of control) | Effect at $10^{-6}$ M (% of control) |
| $E_2$ | 0.01 ± 0 | 4 | 211.6 | 204.7 |
| Ex 23 | 376.5 ± 70.1 | 3 | 81.7 | 175.7 |
| Ex 24 | 18.5 ± 1.8 | 3 | 89.9 | 142.8 |
| Ex 31 | 3.7 ± 0.7 | 4 | 138.8 | 146.3 |
| Ex 35 | 58.2 ± 15.0 | 4 | 94.4 | 162.6 |
| Ex 40 | 11.5 ± 2.8 | 4 | 106.9 | 151.7 |
| Ex 65 | 27.6 ± 2.0 | 4 | 123.1 | 259.5 |
| Ex 66 | 25.4 ± 4.0 | 4 | 100.3 | 148.7 |
| Ex 73 | 365.1 ± 126.1 | 4 | 94.2 | 133.7 |
| Ex 80 | 45.2 ± 25.6 | 4 | 109.5 | 147.2 |
| Ex 81 | 634.8 ± 284.9 | 4 | 86.8 | 117.3 |
| Ex 84 | 77.9 ± 4.1 | 4 | 97.0 | 285.8 |
| Ex 86 | 465.7 ± 34.0 | 4 | 85.6 | 139.4 |
| Ex 93 | 16.1 ± 2.6 | 4 | 115.8 | 155.8 |

Estrogenic Activity In Vivo

Prepubescent female rats were orally treated at 3 mg/rat/day for 3 days. On the day following the last treatment, uteri were removed and wet weights were recorded.

The results are expressed as % of stimulation of uterus weight in comparison with vehicles.

The compounds of examples 23, 31, 35, 66, 73, 84, 86 and 93 exhibited a marked selectivity for the human recombinant estrogen receptor β and a weak estrogenic effect in alkaline phosphatase activity in the Ishikawa cell model.

These compounds were accordingly selected to check their in vitro estrogenicity. The aim of this study was to test these compounds in comparison with tamoxifen (TAM), with an ERβ selective standard agonist: DPN or 2,3-bis-(4-hydroxyphenyl)propionitrile (Meyers M J, J Med Chem 2001, 44; 24, 4230-4251) and with an ERα selective standard agonist: PPT or 1,3,5-tris-(4-hydroxyphenyl)-4-propyl-1H-pyrazole (Stauffer S R, J Med Chem 2000, 43; 4934-4947), when 17β-estradiol (E2) at 3 mg/rat/day p.o. is taken as the standard reference.

TABLE 4

Estrogenic activity of in vitro selected compounds

| Compound | % stimulation vs vehicle | Number of animals |
|---|---|---|
| DPN | 358 | 8 |
| $E_2$ | 526 | 8 |
| Ex 23 | 12 | 8 |
| Ex 24 | 101 | 8 |
| Ex 31 | 468 | 6 |
| Ex 35 | 38 | 8 |
| Ex 40 | 41 | 8 |
| Ex 65 | 84 | 8 |
| Ex 66 | 31 | 8 |
| Ex 73 | 52 | 8 |
| Ex 80 | 70 | 8 |
| Ex 81 | 49 | 8 |
| Ex 84 | 24 | 8 |
| Ex 86 | 25 | 8 |
| Ex 93 | 88 | 8 |
| PPT | 96 | 6 |
| TAM | 206 | 8 |

These results show that the compound of Example 23 is a potent ligand to estrogen receptor beta, with a weak in vivo estrogenic activity after oral administration.

Dose-Related Uterotrophic Activity In Vivo

Prepubescent female rats were orally treated with 0.3; 1; 3 or 10 mg/rat/day for 3 days. On the day following the last treatment, uteri were removed and wet weights were recorded.

The results are expressed as % of stimulation of uterus weight in comparison with vehicles. 17β-estradiol (E2) at 3 mg/rat/day p.o. is taken as the standard reference.

TABLE 5

Dose-related uterotrophic activity in vivo

| Compound | Dosage (mg/rat/day) | % stimulation vs vehicle | Number of animals |
|---|---|---|---|
| $E_2$ | 3 | 333 | 8 |
| Ex 23 | 0.3 | −13 | 8 |
| Ex 23 | 1 | −5 | 8 |
| Ex 23 | 3 | −4 | 8 |
| Ex 23 | 10 | 20 | 8 |

The compound of example 23 has been selected as a potential good candidate for treating estrogenic dependent diseases because of the lack of uterotrophicity up to a 3 mg/animal/day dosage, after oral administration.

Effect of Compounds on Hot Flush Model In Vivo

According to Berendsen et al. (Eur. J. Pharmacol., 2003, 482; 329-33), tail skin temperature of ovariectomized rats may serve as a useful tool for selection of compounds that are of potential use in the treatment of hot flushes in postmenopausal women. The aim of this study was to evaluate the effect of the compound of Example 23 over 4 days on tail skin temperature in ovariectomized rats. 17β-estradiol, the standard reference, was administered by oral route at 1 mg/rat/day over 13 consecutive days (Watanabe N. et al, 2003). Twenty IOPS Wistar female rats from Charles River France, weighing 176 to 200 g on arrival, were used for the study. Rats were accommodated in groups of four in stainless steel mesh cages. After implantation of telemetric transmitters (TA10TA-F40, Data Sciences International) until the end of the study, they were housed in groups of two in macrolon cages and maintained on a 14-10 hours light/dark cycle. Standard environmental conditions for this species were regularly controlled.

Animals were allowed free access to a specific estrogen-free diet of Harlan Teklad 2016 pellets from HARLAN. They were allowed free access to filtered and softened tap water. Water was dispensed ad libitum via automatic deliveries in metallic cages and in plastic bottles in macrolon cages. Rats were then ovariectomized and left undisturbed for at least 2 weeks. After this hormonal rest period, tail skin temperature was monitored during the same period and animals were randomized into 3 groups based on mean temperature. The first group was "ovariectomy control group", the second group was "estradiol group" to confirm the estrogen activity on tail temperature and the third group was "Ex 23 group" to test the activity of this product on temperature. Body weights were then recorded on the first day of treatment and at the end of study.

The Results are expressed as % of stimulation of uterus weight in comparison with vehicles. 17β-estradiol (E2) at 3 mg/rat/day is taken as the standard reference.

TABLE 6

Effect of Ex 23 on tail skin temperature (TST) in ovariectomized rats

| Compound | Dosage (mg/rat/day) | TST Variation day 1 vs day 0 (C. °) | TST Variation day 4 vs day 0 (C. °) | TST Variation day 7 vs day 0 (C. °) | n |
|---|---|---|---|---|---|
| vehicle | — | −0.6 | −0.6 | −0.7 | 4 |
| E$_2$ | 3 | −4.8 | −3.5 | −5.6 | 4 |
| Ex 23 | 0.3 | −0.8 | −2.1 | −1.9 | 10 |

The compound of example 23 decreased tail skin temperature of ovariectomized rat, without deleterious side-effects on uteri, unlike estradiol activity on body weight or uteri (as seen below).

TABLE 7

Effect of Ex 23 on body weight and uteri, after one week treatment

| Compound | Dosage (mg/rat/day) | Uteri weight (% increase vs vehicle) | Body weights (% increase vs vehicle) | n |
|---|---|---|---|---|
| vehicle | — | — | — | 4 |
| E$_2$ | 3 | 273 | −10 | 4 |
| Ex 23 | 0.3 | −2.6 | +4.4 | 10 |

Effect of Compounds on Bone and Cardiovascular Parameters In Vivo

The ovariectomized rat is a mandatory model for preclinical evaluation of new compounds used for the prevention of bone loss (osteoporosis). Female Wistar—derived OFA strain rats from IFFA CREDO (France) were ovariectomized or sham operated as intact control. Upon arrival, they were housed in metal hanging cages in groups of 3 or 4 per cage and had ad libitum access to food and water for one week. After a one week acclimation period, daily dosing was carried out with the compound of interest or 17β-estradiol.

During the study, plasma samples were taken to allow lipid parameter assay: triglycerides, free cholesterol, total cholesterol, HDL, LDL, VLDL, apoliporotein A and B100; bone metabolism parameters such as: DPD, $Ca^{2+}$, collagen type I and II C-telopeptide fragments; and urinary bone markers such as $Ca^{2+}$, and inorganic phosphate. All assays were carried out following the manufacturer's recommendations.

To allow bone mineral density measurement of individual lumbar segments, lumbar high resolution or whole body dual energy X-ray absorptiometry procedures were carried out during the study on isoflurane anesthetized animals.

Antidepressant Activity of Compounds

Antidepressant effect of estradiol was recently reported in studies using ER β KO mice model. In addition, ER β localization in dorsal raphe nucleus area in rat has been described. The gold standard test for antidepressant potency of compound consist in the forced swimming test, in this experiment antidepressants could be distinguished from psychostimulants which decreased immobility at doses which increased general activity. In order to investigate the putative antidepressant potency of the compounds reported here, the forced swimming test was performed according to the following design. The animals were housed six per cage under standard colony conditions, with a 12 h light/dark cycle and ad libitum food and water. They were allowed to acclimatize to the colony for at least 7 days prior to any experimentation. For subcutaneous administration, the compound of Example 23 was dissolved in olive oil and diluted to the desired concentration on the day of administration. For positive control, intraperitoneal (i.p.) injection of desipramine was done. Desipramine was dissolved in double-distilled water (10 mg/kg). The experiments were conducted 30 min after the positive control drug treatment (only for desipramine treatment). Other compounds, ie: estradiol and the compound of Example 23 were daily injected subcutaneously in rats, during a 7 days period. Acquisition were performed on day 8 (24 h after the last administration of items) and day 9 (48 h after estradiol or compound 23 administration), respectively. Data acquired 24 hours after the last administration consisted in the "naïve animal group", these animals had never been previously tested in the device. Data acquired 48 hours after a last administration of compounds consisted in "trained animal group".

TABLE 8

Effect of Ex 23 onto immobility duration in stress conditions

| Compound | Dosage (mg/rat/day) | Naïve animals (s.) | Trained animals (s.) | n |
|---|---|---|---|---|
| vehicle | — | 133.7 ± 28.6 | 178.1 ± 25.5 | 11 |
| desipramine | 30 | Not tested | 2.6 ± 1.5*** | 11 |
| E2 | 0.007 | 22.5 ± 7.1*** | 79.2 ± 23.0* | 11 |
| Ex 23 | 2.8 | 45.2 ± 15.6* | 160.7 ± 44.1 | 12 |

(acquisition during a 10 minutes test, items or desipramine vs vehicle, $p < 0.05$, $p < 0.001$)

On the 8th, the forced swim test was performed. This study was carried out in rats according to the methods described by Porsolt (Eur. J. Pharm., 1978). Briefly, rats were placed individually in glass cylinders (height: 40 cm, diameter: 18 cm) containing 25 cm of water at 25° C. Ten minutes later, rats were removed and dried before being returned to their home cages. The animals were replaced in the cylinders 24 h later, and the procedure was repeated, and a 10-min observation period was recorded.

The model was validated by desipramine activity found in the test. Results shown the confirmation of the antidepressor potency of estradiol, 24 h and 48 h after administration. the compound of Example 23 exhibited a antidepressor activity when animals were first-in-the-test 24 h after administration, while in trained animal group 48 h after administration, the antidepressor potency of the compound of Example 23 disappeared.

The invention claimed is:

1. A compound selected from:
   3-cyclopentyl-1H-indazol-6-ol;
   3-cyclohexyl-1H-indazol-6-ol;
   1-(aminosulfonyl)-3-cyclohexyl-1H-indazol-6-yl-sulfamate;
   3-cyclohexyl-6-hydroxy-1H-indazole-1-sulfonamide;
   2-(6-hydroxy-1,2-benzisoxazol-3-yl)-3-(4-hydroxyphenyl)propanenitrile;
   2-(6-hydroxy-1,2-benzisoxazol-3-yl)-3-(3-fluoro-4-hydroxyphenyl)propanenitrile;
   2-(6-hydroxy-1,2-benzisoxazol-3-yl)-3-(4-fluorophenyl)propanenitrile;
   2-(6-hydroxy-1,2-benzisoxazol-3-yl)-3-(3,4-dihydroxyphenyl)propanenitrile;
   or pharmaceutically acceptable salts thereof.

2. A compound according to claim 1, which is 3-cyclopentyl-1H-indazol-6-ol or a pharmaceutically acceptable salt thereof.

3. A pharmaceutical composition comprising (i) a compound according to claim 1 or a pharmaceutically acceptable salt thereof and (ii) a pharmaceutically acceptable excipient.

4. A pharmaceutical composition comprising (i) a compound according to claim 2 or a pharmaceutically acceptable salt thereof and (ii) a pharmaceutically acceptable excipient.

5. Method for the treatment of any one of hot flushes, of osteoporosis, of control or management of female fertility, of breast tumors, or of polycystic ovary syndrome,
   which comprises administering to a subject in need thereof a therapeutically effective amount of a compound according to claim 1 or a pharmaceutically acceptable salt thereof.

* * * * *